(12) United States Patent
Lopato et al.

(10) Patent No.: US 8,822,759 B2
(45) Date of Patent: Sep. 2, 2014

(54) GL9 TRANSCRIPTIONAL CONTROL SEQUENCES

(75) Inventors: Sergiy Lopato, Morphett Vale (AU); Nataliya Kovalchuk, Brompton (AU)

(73) Assignee: Australian Centre for Plant Functional Genomics Pty. Ltd., Urrbrae (AU)

(*) Notice: Subject to any disclaimer, the term of this patent is extended or adjusted under 35 U.S.C. 154(b) by 448 days.

(21) Appl. No.: 13/051,853

(22) Filed: Mar. 18, 2011

(65) Prior Publication Data

US 2011/0231954 A1 Sep. 22, 2011

(30) Foreign Application Priority Data

Mar. 18, 2010 (AU) ................................ 2010901142

(51) Int. Cl.
*C07H 21/04* (2006.01)
*C12N 15/113* (2010.01)
*C12N 15/63* (2006.01)
*C12N 15/82* (2006.01)

(52) U.S. Cl.
USPC ........... 800/287; 800/278; 800/298; 800/320; 435/410; 435/419; 536/24.1

(58) Field of Classification Search
None
See application file for complete search history.

(56) References Cited

PUBLICATIONS

Nakamura et al. Characterization of the class IV homeodomain-leucine zipper gene family in *Arabidopsis*. Plant Physiology. 2006. 141: 1363-1375.*
Kim et al. A 20 nucleotide upstream element is essential for the nopaline synthase (nos) promoter activity. Plant Molecular Biology. 1994. 24: 105-117.*
Yang et al. OSTF1: a HD-GL2 family homeobox gene is developmentally regulated during early embryogenesis in rice. Plant Cell Physiology. 2002. 43(6): 628-638.*
GenBank Accession No. TF1_ORYSJ. Homeobox-leucine zipper protein TF1. published Mar. 3, 2009.*
Lamacchia et al. Endosperm-specific activity of a storage protein gene promoter in transgenic wheat seed. Journal of Experimental Botany. 2001. 52(355): 243-250.*
Baumlein et al. Cis-analysis of a seed protein gene promoter: the conservative RY repeat CATGATG within the legumin box is essential for tissue-specific expression of a legumin gene. The Plant Journal. 1992. 2(2): 233-239.*

* cited by examiner

*Primary Examiner* — Brent T Page
*Assistant Examiner* — Ashley K Buran
(74) *Attorney, Agent, or Firm* — Klarquist Sparkman, LLP

(57) ABSTRACT

The present invention relates to transcriptional control sequences derived from GL9 genes, wherein the transcriptional control sequences direct specific or preferential expression of an operably connected nucleotide sequence of interest in one or more parts of a plant seed.

15 Claims, 6 Drawing Sheets

GL9 TRANSCRIPTIONAL CONTROL SEQUENCES

CROSS-REFERENCES TO RELATED APPLICATIONS

This application claims priority to Australian provisional patent application 2010901142, filed 18 Mar. 2010, the contents of which are herein incorporated by this reference.

BACKGROUND OF THE INVENTION

The present invention relates generally to transcriptional control sequences for effecting expression of a nucleotide sequence of interest in a plant. More particularly, the present invention relates to transcriptional control sequences that direct specific or preferential expression of an operably connected nucleotide sequence of interest in one or more parts of a plant seed.

Expression of a DNA sequence in a plant is dependent, in part, upon the presence of an operably linked transcriptional control sequence, such as a promoter or enhancer, which is functional within the plant. The transcriptional control sequence determines when and where within the plant the DNA sequence is expressed. For example, where continuous expression is desired throughout the cells of a plant, constitutive promoters are utilised. In contrast, where gene expression in response to a stimulus is desired, an inducible promoter may be used. Where expression in specific tissues or organs is desired, a tissue-specific promoter may be used.

Accordingly, there is a substantial interest in identifying transcriptional control sequences, such as promoters or enhancers, which are active in plants. Frequently, it is also desirable to specifically or preferentially direct transcription in particular plant organs, tissues or cell types, or at particular developmental stages of plant growth. Thus, isolation and characterisation of transcriptional control sequences, which can serve as regulatory regions for the expression of nucleotide sequences of interest in particular cells, tissues or organs of a plant, would be desirable for use in the genetic manipulation of plants.

Reference to any prior art in this specification is not, and should not be taken as, an acknowledgment or any form of suggestion that this prior art forms part of the common general knowledge in any country.

BRIEF SUMMARY OF THE INVENTION

In a first aspect, the present invention provides an isolated nucleic acid comprising:

(i) a nucleotide sequence defining a transcriptional control sequence which specifically or preferentially directs expression of an operably connected nucleotide sequence in one or more parts of a plant seed, wherein said transcriptional control sequence is derived from a GL9 gene; and/or (ii) a nucleotide sequence defining a functionally active fragment or variant of the nucleotide sequence defined at (i).

In some embodiments, the transcriptional control sequence directs expression of an operably connected nucleotide sequence in one or more parts of a seed of a monocotyledonous plant. In some embodiments, the monocotyledonous plant is a plant in the family Poaceae. In some embodiments, the monocotyledonous plant is a cereal crop plant. In some embodiments, the cereal crop plant is a wheat plant, a barley plant or a rice plant.

In some embodiments, the transcriptional control sequence directs expression of an operably connected nucleotide sequence in the embyro, or a part thereof, in the seed. In some embodiments, the transcriptional control sequence directs expression of an operably connected nucleotide sequence in the endosperm, or a part thereof, in the seed.

In some embodiments, the transcriptional control sequence is derived from a monocotyledonous plant. In some embodiments, the transcriptional control sequence is derived from a plant in the family Poaceae. In some embodiments, the transcriptional control sequence is derived from a cereal crop plant. In some embodiments, the transcriptional control sequence is derived from a *Triticum* sp. Plant. In some embodiments, the transcriptional control sequence is derived from a *Triticum durum* plant.

In some embodiments, the GL9 gene encodes a GL9 polypeptide which comprises the amino acid sequence set forth in SEQ ID NO: 1 or a homolog thereof. In some embodiments, the homolog comprises at least 80% amino acid sequence identity to SEQ ID NO: 1.

In some embodiments, the transcriptional control sequence is derived from a gene which comprises an open reading frame comprising the nucleotide sequence set forth in SEQ ID NO: 2, or a homolog thereof. In some embodiments, the transcriptional control sequence is derived from a gene which comprises the nucleotide sequence set forth in SEQ ID NO: 4, or a homolog thereof. In some embodiments, the transcriptional control sequence comprises the nucleotide sequence set forth in SEQ ID NO: 3 or a functionally active fragment or variant thereof.

In a second aspect, the present invention provides a nucleic acid construct comprising the isolated nucleic acid according to the first aspect of the invention. In some embodiments, the nucleic acid construct further comprises a nucleotide sequence of interest operably connected to the nucleic acid according to the first aspect of the invention. In some embodiments, the nucleotide sequence of interest is heterologous with respect to the nucleic acid according to the first aspect of the invention.

In a third aspect, the present invention provides a cell comprising a nucleic acid construct according to the second aspect of the invention. In some embodiments, the cell is a plant cell. In some embodiments, cell is a monocotyledonous plant cell. In some embodiments, cell is a cell from a plant in the family Poaceae. In some embodiments, the cell is a cereal crop plant cell. In some embodiments, the cell is a wheat cell, a barley cell or a rice cell.

In a fourth aspect, the present invention provides a multicellular structure comprising one or more cells according to the third aspect of the invention. In some embodiments, the multicellular structure comprises a plant or a part, organ or tissue thereof. In some embodiments, the plant or a part, organ or tissue thereof comprises a seed or a part thereof.

In a fifth aspect, the present invention provides a method for specifically or preferentially expressing a nucleotide sequence of interest in one or more parts of a plant seed, the method comprising effecting transcription of the nucleotide sequence of interest in a plant under the transcriptional control of a nucleic acid according to a first aspect of the invention. In some embodiments, the plant is a monocotyledonous plant. In some embodiments, the plant is a plant in the family Poaceae. In some embodiments, the plant is a cereal crop plant. In some embodiments, the plant is a wheat plant, a barley plant or a rice plant.

In some embodiments, the transcriptional control sequence directs expression of an operably connected nucleotide sequence in the embyro, or a part thereof, in the seed. In some embodiments, the transcriptional control sequence directs expression of an operably connected nucleotide sequence in the endosperm, or a part thereof, in the seed. In some embodiments, the nucleotide sequence of interest is heterologous with respect to the transcriptional control sequence.

DETAILED DESCRIPTION OF THE INVENTION

Figure 1:
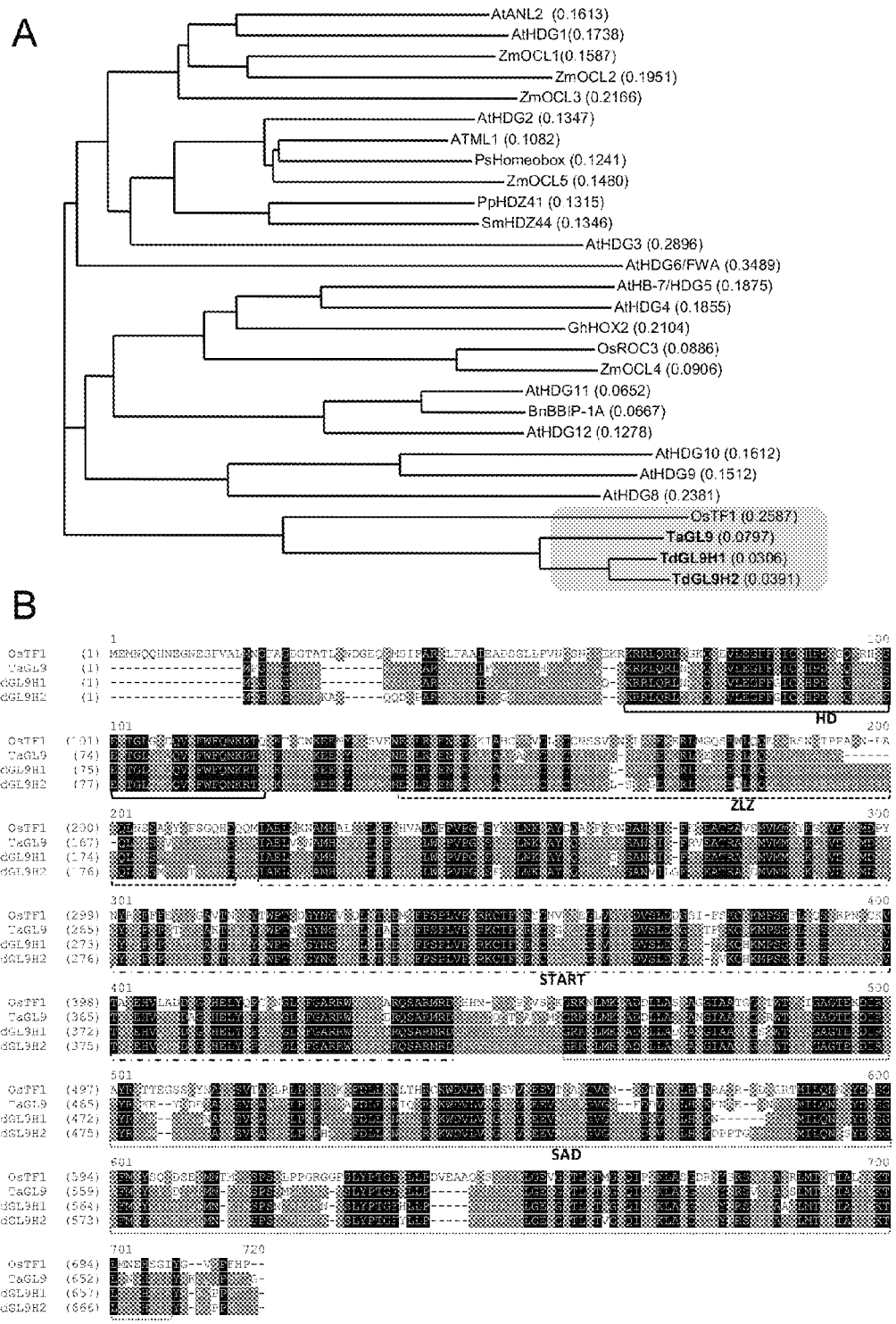
FIG. 1A shows a phylogenetic tree of the amino acid sequences of TaGL9, TdGL9L (TdGL9H1), TdGL9H2 and known and putative HDZipIV homologues from other plants. Genbank accession numbers for each putative HD Zip IV homolog are as follows: AtANL2 (Acc. NP_567183), AtHDG1 (Acc. NP_191674), ZmOCL1 (Acc. CAG38614), ZmOCL2 (Acc. CAB96422), ZmOCL3 (Acc. CAB96423), AtHB-7/HDG5 (Acc. Q9FJS2), AtHDG4 (Q8L7H4), GhHOX2 (Acc. AAM97322), OsROC3 (Acc. A2ZAI7), ZmOCL4 (Acc. CAB96424), AtHDG11 (Acc. NP_177479), BnBBIP-1A (Acc. ABA54874), AtHDG12 (Acc. NP_564041), AtHDG10 (Acc. NP_174724), AtHDG9 (Acc. NP_197234), AtHDG8 (Acc. Q9M9P4), OsTF1 (Acc. Q5ZAY0), AtHDG6/FWA (Acc. Q9FVI6), AtHDG2 (Acc. Q94C37), ATML1 (Acc. AL161555), PsHomeobox (Acc. AAB37230), ZmOCL5 (Acc. CAB96425), PpHDZ41 (Acc. DAA05775), SmHDZ44 (Acc. DAA05774), AtHDG3 (Acc. Q9ZV65). The GL9 Glade is marked with a grey box; names of wheat proteins are in bold. TaGL9, TdGL9L and TdGL9H2 form a distinct subgroup.
FIG. 1B shows an alignment of the amino acid sequences of TaGL9, TdGL9L (TdGL9H1) and TdGL9H2 to OsTF1. Identical amino acids are in black boxes, similar amino acids are in grey boxes. The main protein domains are underlined: HD—homeodomain, ZLZ—leucine zipper, START—steroidogenic acute regulatory protein-related lipid transfer domain, and SAD—START associated conserved domain. Sequences of TaGL9 and TdGL9L are 83.0% identical. Sequences of TdGL9H2 and TdGL9L are 91.4% identical. Sequences of TaGL9 and TdGL9H2 are 80.9% identical. The protein sequence of OsTF1 has 46.5%, 46.2% and 46.8% identity to TdGL9L, TaGL9, and TdGL9H2, respectively.

Nucleotide and amino acid sequences are referred to herein by a sequence identifier number (SEQ ID NO:). A summary of the sequence identifiers is provided in Table 1. A sequence listing is provided at the end of the specification.

TABLE 1

SUMMARY OF SEQUENCE IDENTIFIERS

| Sequence Identifier | Sequence |
|---|---|
| SEQ ID NO: 1 | TdGL9L (TdGL9H1) protein amino acid sequence |
| SEQ ID NO: 2 | TdGL9L (TdGL9H1) cDNA nucleotide sequence |
| SEQ ID NO: 3 | TdGL9L (TdGL9H1) promoter nucleotide sequence |
| SEQ ID NO: 4 | TdGL9L (TdGL9H1) gene nucleotide sequence |
| SEQ ID NO: 5 | TdGL9L (TdGL9H1) promoter and gene nucleotide sequence |
| SEQ ID NO: 6 | TaGL9 protein amino acid sequence |
| SEQ ID NO: 7 | TaGL9 cDNA nucleotide sequence |
| SEQ ID NO: 8 | prolamin box nucleotide sequence |
| SEQ ID NO: 9 | RY repeat motif nucleotide sequence |
| SEQ ID NO: 10 | binding site for embryo specific bZIP transcription factor |
| SEQ ID NO: 11 | E-box nucleotide sequence |
| SEQ ID NO: 12 | S-box nucleotide sequence |
| SEQ ID NO: 13 | A-box nucleotide sequence |
| SEQ ID NO: 14 | pyrimidin box nucleotide sequence |
| SEQ ID NO: 15 | bait repeat nucleotide sequence |
| SEQ ID NO: 16 | TdGL9H2 protein amino acid sequence |
| SEQ ID NO: 17 | TdGL9H2 cDNA nucleotide sequence |

A new HDZipIV gene from wheat, designated *Triticum aestivum* GLABRA2 like clone 9 (TaGL9), has been isolated in a Y1H screen of a cDNA library prepared from wheat grain at 0-6 days after pollination (DAP). The 3'-untranslated region of TaGL9 was used as a probe to isolate a genomic clone of a homologous/orthologous gene (designated TdGL9L), and a cDNA clone of a homologous/orthologous gene (designated TdGL9H2) from a BAC library prepared from *Triticum durum*. Spatial and temporal expression patterns of TaGL9 and TdGL9L (also referred to herein as "TdGL9H1") were examined by quantitative real time PCR (Q-PCR) and revealed seed specific expression of these genes. A TdGL9L promoter-GUS fusion construct was generated and was used for stable transformation of wheat, barley and rice plants. Whole-mount and histochemical GUS staining patterns revealed seed specific activity of TdGL9L promoter in transgenic plants. Gus expression was initially detected between 3 and 8 days after pollination (DAP) in embryos at the globular stage and adjacent to the embryo fraction of the endosperm. Expression was strongest in the outer layers of the embryo. In developed embryos, TdGL9L promoter activity was observed primarily in the main vascular bundle of the scutellum. TdGL9L promoter activity was also observed in vascular bundles of embryonic coleoptiles and leaves in rice seed.

As used herein, the term "transcriptional control sequence" should be understood as a nucleotide sequence that modulates at least the transcription of an operably connected nucleotide sequence. As such, the transcriptional control sequences of the present invention may comprise any one or more of, for example, a leader, promoter, enhancer or upstream activating sequence. As referred to herein, the term "transcriptional control sequence" preferably at least includes a promoter. A "promoter" as referred to herein, encompasses any nucleic acid that confers, activates or enhances expression of an operably connected nucleotide sequence in a cell.

As used herein, the term "operably connected" refers to the connection of a transcriptional control sequence, such as a promoter, and a nucleotide sequence of interest in such a way as to bring the nucleotide sequence of interest under the transcriptional control of the transcriptional control sequence. For example, promoters are generally positioned 5' (upstream) of a nucleotide sequence to be operably connected to the promoter. In the construction of heterologous transcriptional control sequence/nucleotide sequence of interest combinations, it is generally preferred to position the promoter at a distance from the transcription start site that is approximately the same as the distance between that promoter and the gene it controls in its natural setting, i.e. the gene from which the promoter is derived. As is known in the art, some variation in this distance can be accommodated without loss of promoter function.

Thus, in a first aspect, the present invention provides an isolated nucleic acid comprising:

(i) a nucleotide sequence defining a transcriptional control sequence which specifically or preferentially directs expression of an operably connected nucleotide sequence in one or more parts of a plant seed, wherein said transcriptional control sequence is derived from a GL9 gene; and/or (ii) a nucleotide sequence defining a functionally active fragment or variant of the nucleotide sequence defined at (i).

In the present invention, "isolated" refers to material removed from its original environment (e.g. the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. An "isolated" nucleic acid molecule should also be understood to include a synthetic nucleic acid molecule, including those produced by chemical synthesis using known methods in the art or by in-vitro amplification (e.g. polymerase chain reaction and the like).

The isolated nucleic acid of the present invention may comprise any polyribonucleotide or polydeoxyribonucleotide, which may be unmodified RNA or DNA or modified RNA or DNA. For example, the isolated nucleic acid molecules of the invention may comprise single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the isolated nucleic acid molecules may comprise triple-stranded regions comprising RNA or DNA or both RNA and DNA. The isolated nucleic acid molecules may also contain one or more modified bases or DNA or RNA backbones modified for stability or for other reasons. "Modified" bases include, for example, tritylated bases and unusual bases such as inosine. A variety of modifications can be made to DNA and RNA; thus the term "nucleic acid" also embraces chemically, enzymatically, or metabolically modified forms of DNA and RNA.

As set out above, the method of the present invention contemplates a transcriptional control sequence which specifically or preferentially directs expression of an operably connected nucleotide sequence in one or more parts of a plant seed.

As referred to herein, a plant "seed" should be understood to refer to a mature or immature plant seed. As such, the term "seed" includes, for example, immature seed carried by a maternal plant or seed released from the maternal plant. In some embodiments, the term "seed" may encompass any seed plant sporophyte between the developmental stages of fertilisation and germination.

As would be appreciated, the term "seed" may also encompass the various cells and tissues that make up the mature or immature seed. For example, mature seeds may include tissue types such as the embryo, embryo surrounding region, endosperm transfer layer, starchy endosperm, aleurone layer, pericarp and the like. Meanwhile, immature seeds may include, for example, fertilised egg cells, zygotes, fertilised central cells, embryos, the endosperm coenocyte, the endosperm syncytium and the like.

In some embodiments, the term "seed" may also extend to floral and/or maternal gametophyte tissues. For example, the term "seed" may include floral and/or maternal gametophyte structures that are precursors to, and/or ultimately develop into, a seed or an associated structure. An example of such a structure may include an ovary or embryo sac in a plant flower.

It should be understood that reference herein to expression in a plant seed refers to the transcription and/or translation of a nucleotide sequence in one or more cells or tissues of a plant seed and/or at one or more developmental stages of the plant seed. This definition in no way implies that expression of the nucleotide sequence must occur in all cells of the plant seed or at all developmental stages of the seed. As set out later, the nucleic acids of the present invention may direct expression in particular parts of a seed and/or at particular developmental stages of a seed.

As set out above, the transcriptional control sequences contemplated by the present invention "specifically or preferentially" direct expression of an operably connected nucleotide sequence in a plant seed. As used herein, "specifically expressing" means that the nucleotide sequence of interest is expressed substantially only in a plant seed (or a particular tissue or cell type therein). "Preferentially expressing" should be understood to mean that the nucleotide sequence of interest is expressed at a higher level in a plant seed (or tissue or cell type therein) than in one or more other tissues of the plant, e.g. leaf tissue or root tissue. In some embodiments "preferential" expression in a plant flower includes expression of a nucleotide sequence of interest in a plant seed (or a tissue or cell type therein) at a level of, for example, at least twice, at least 5 times or at least 10 times the level of expression seen in at least one other non-seed tissue of the plant.

The transcriptional control sequence or functionally active fragment or variant thereof may effect specific or preferential expression in a seed from at least one seed plant species, including monocotyledonous angiosperm plants ("monocots"), dicotyledonous angiosperm plants ("dicots") or gymnosperm plants. For clarity, this should be understood as the transcriptional control sequence or functionally active fragment or variant thereof being able to effect specific or preferential expression in a seed in at least one plant species. The transcriptional control sequence may or may not effect expression in one or more other plant species, and this expression may or may not be specific or preferential to the seed. Thus, the transcriptional control sequences of the present invention need not be active in all plant species, and need not necessarily direct specific or preferential expression in the seed in all plants in which they are active.

In some embodiments, the transcriptional control sequence directs expression of an operably connected nucleotide sequence in one or more parts of a seed of a monocotyledonous plant.

In some embodiments, the transcriptional control sequence directs expression of an operably connected nucleotide sequence in one or more parts of a seed of a plant in the family Poaceae.

In some embodiments, the transcriptional control sequence directs expression of an operably connected nucleotide sequence in one or more parts of a seed of a cereal crop plant.

As used herein, the term "cereal crop plant" may be a member of the Poaceae (grass family) that produces grain. Examples of Poaceae cereal crop plants include wheat, rice, maize, millets, sorghum, rye, triticale, oats, barley, teff, wild rice, spelt and the like. The term cereal crop plant should also be understood to include a number of non-Poaceae plant species that also produce edible grain, which are known as the pseudocereals and include, for example, amaranth, buckwheat and quinoa.

In some embodiments, the transcriptional control sequence directs expression of an operably connected nucleotide sequence in one or more parts of a seed of a wheat plant.

As referred to herein, "wheat" should be understood as a plant of the genus *Triticum*. Thus, the term "wheat" encompasses diploid wheat, tetraploid wheat and hexaploid wheat. In some embodiments, the wheat plant may be a cultivated species of wheat including, for example, *T. aestivum, T. durum, T. monococcum* or *T. spelta*. In some embodiments, the term "wheat" refers to wheat of the species *Triticum aestivum*.

In some embodiments, the transcriptional control sequence directs expression of an operably connected nucleotide sequence in one or more parts of a seed of a barley plant.

As referred to herein, "barley" includes several members of the genus *Hordeum*. The term "barley" encompasses cultivated barley including two-row barley (*Hordeum distichum*), four-row barley (*Hordeum tetrastichum*) and six-row barley (*Hordeum vulgare*). In some embodiments, barley may also refer to wild barley, (*Hordeum spontaneum*). In some embodiments, the term "barley" refers to barley of the species *Hordeum vulgare*.

In some embodiments, the transcriptional control sequence directs expression of an operably connected nucleotide sequence in one or more parts of a seed of a rice plant.

As referred to herein, "rice" includes several members of the genus *Oryza* including the species *Oryza sativa* and *Oryza glaberrima*. The term "rice" thus encompasses rice cultivars such as japonica or sinica varieties, indica varieties and javonica varieties. In some embodiments, the term "rice" refers to rice of the species *Oryza sativa*.

As set out above, the nucleic acid of the first aspect of the present invention may also specifically or preferentially direct expression in a particular cell or tissue of a plant seed and/or specifically or preferentially direct expression at a particular developmental stage of a plant seed.

In some embodiments, the transcriptional control sequence directs expression of an operably connected nucleotide sequence in the embyro, or a part thereof, in the seed.

As referred to herein, the "embryo" of a plant seed refers to the part of a seed that comprises the precursor tissues of the leaves, stem (ie. hypocotyl), and root (ie. radicle), as well as one or more cotyledons. The number of cotyledons comprised within the embryo can vary according to the plant taxon. For example, dicotyledonous angiosperm embryos comprise two cotyledons, monocotyledonous angiosperm embryos comprise a single cotyledon (also referred to as the scutellum), while gymnosperm embryos may comprise a variable number of cotyledons, typically ranging from 2 to 24. In light of the above, reference herein to an "embryo", particularly in the context of specific or preferential expression within an embryo (see later), may include expression in all of the embryo or expression in one or more cells, tissues or parts of the embryo.

In some embodiments, the transcriptional control sequence directs expression of an operably connected nucleotide sequence in one or more of the globular embryo, the outer cell layers of an embryo, a cotyledon or scutellum of the embryo and/or a vascular bundle of the embryo, including the main vascular bundle of the scuttelum, and/or the vascular bundles of the coleoptile and embryonic leaves.

In some embodiments, the transcriptional control sequence directs expression of an operably connected nucleotide sequence in the endosperm, or a part thereof, in the seed.

The tissues of a plant encompassed by the term "endosperm" would be readily understood by one of skill in the art. However, this term should be understood to encompass at least the nutritive tissue, characteristic of flowering plants, which nourishes the embryo. The endosperm is typically formed after the fertilisation of the polar nuclei of the central cell by a sperm nucleus. In most plants the endosperm is a transient tissue absorbed by the embryo before maturity, whereas in cereals and grasses it contains storage reserves in the mature grain and is not absorbed until after germination.

Typically, the "endosperm" includes at least five cell types, namely, the central starchy endosperm (CSE), the sub-aleurone layer (SAL), the aleurone layer (AL), the endosperm transfer layer (ETL) and the embryo-surrounding region (ESR). The characteristics of each of these cell types are described in detail in the review of Olsen et al., 1999, *Trends in Plant Science* 4(7): 253-257.

In some embodiments, the transcriptional control sequence directs expression of an operably connected nucleotide sequence in the embryo surrounding region of the endosperm in a seed.

As set out above, the present invention contemplates a transcriptional control sequence which specifically or preferentially directs expression of an operably connected nucleotide sequence in one or more parts of a plant seed, wherein said transcriptional control sequence is derived from a GL9 gene.

The term "derived from", as used herein, refers to a source or origin for the transcriptional control sequence. For example, a transcriptional control sequence "derived from a GL9 gene" refers to a transcriptional control sequence which, in its native state, exerts at least some transcriptional control over a GL9 gene. The term "derived from" should also be understood to refer to the source of the sequence information for a transcriptional control sequence and not limited to the source of a nucleic acid itself. Thus, a transcriptional control sequence derived from a GL9 gene need not necessarily be directly isolated from the gene. For example, a synthetic nucleic acid having a sequence that is determined with reference to a transcriptional control sequence which, in its native state, exerts at least some transcriptional control over a GL9 gene should be considered derived from a GL9 gene.

A "GL9 gene" as referred to herein encompasses any nucleotide sequence which encodes a GL9 polypeptide. As described later, GL9 polypeptides may be characterised as members of the class IV of homeodomain leucine zipper family of transcription factors.

In many eukaryotic organisms including higher plants, transcription factors which contain a 60 amino acid long conserved sequence, known as a homeodomain (HD) or homeobox, are important regulators of development. Plant homeodomain transcription factors were originally divided into 5 families: HD-ZIP, GLABRA, KNOTTED, PHD and BEL. However, recent analysis of all homeodomain containing sequences present in sequenced genomes resulted in the identification of a larger number of families and subfamilies. One of the largest families, the HD-ZIP family, is a group of transcription factors containing a homeodomain (HD) together with a leucine zipper (ZIP) motif. The HD-ZIP transcription factors have been classified into four classes of protein (I-IV). The class IV HD-ZIP proteins are also known as the HD-GL2 family after the first identified gene from *Arabidopsis*, GLABRA2 (GL2).

In some embodiments, a GL9 polypeptide may be a class IV HD-ZIP transcription factor.

The class IV HD-Zip family of transcription factors are characterised by four well defined domains:
 a DNA binding homeodomain;
 a leucine zipper domain (for dimerisation);
 a STeroidogenic Acute Regulatory protein-related lipid Transfer (START) domain; and
 a START associated conserved domain (HD-SAD).

In some embodiments, the GL9 polypeptide encoded by the GL9 gene contemplated in accordance with the present invention comprises the amino acid sequence set forth in SEQ ID NO: 1 or a homolog thereof.

The term "homolog", as used herein with reference to homologs of polypeptides comprising the amino acid sequence set forth in SEQ ID NO: 1, should be understood to include, for example, homologs, orthologs, paralogs, mutants and variants of polypeptides comprising the amino acid sequence set forth in SEQ ID NO: 1. In some embodiments, the homolog, ortholog, paralog, mutant or variant of a polypeptide comprising the amino acid sequence set forth in SEQ ID NO: 1 comprises an amino acid sequence which comprises at least 35% sequence identity, at least 40% sequence identity, at least 45% sequence identity, at least 50% sequence identity, at least 55% sequence identity, at least 60% sequence identity, at least 65% sequence identity, at least 70% sequence identity, at least 75% sequence identity, at least 80% sequence identity, at least 85% sequence identity, at least 90% sequence identity or at least 95% sequence identity to the amino acid sequence set forth in SEQ ID NO: 1.

When comparing amino acid sequences to calculate a percentage identity, the compared sequences should be compared over a comparison window of at least 100 amino acid residues, at least 200 amino acid residues, at least 400 amino acid residues, at least 800 amino acid residues, or over the full length of SEQ ID NO: 1. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerised implementations of algorithms such the BLAST family of programs as, for example, disclosed by Altschul et al., 1997, *Nucl. Acids Res.* 25: 3389-3402. A detailed discussion of sequence analysis can be found in Unit 19.3 of Ausubel et al., 1998, *Current Protocols in Molecular Biology*, John Wiley & Sons Inc, 1994-1998, Chapter 15.

As set out in the examples, TdGL9L (SEQ ID NO: 1), TaGL9 (SEQ ID NO: 6) and TdGL9H2 (SEQ ID NO: 16) were found to form a divergent group within the class IV HD-Zip family, and these sequences were found to share a high level of amino acid sequence identity (83.0% between TdGL9L and TaGL9, 80.9% between TdGL9H2 and TaGL9, and 91.4% between TdGL9L and TdGL9H2). As such, in some embodiments, an example of a homolog of a polypeptide comprising the amino acid sequence set forth in SEQ ID NO: 1 is a polypeptide comprising the amino acid sequence set forth in SEQ ID NO: 6 or SEQ ID NO: 16. Also, in some embodiments, reference herein to a homolog of a polypeptide comprising the amino acid sequence set forth in SEQ ID NO: 1 specifically includes polypeptides comprising at least 80% sequence identity to SEQ ID NO: 1.

The transcriptional control sequence of the present invention may be derived from any source, including isolated from any suitable organism or they may be synthetic nucleic acid molecules.

In some embodiments the transcriptional control sequence contemplated herein is derived from a plant. In some embodiments, the transcriptional control sequence of the present invention is derived from a monocotyledonous plant species. In some embodiments the transcriptional control sequence of the present invention is derived from a plant in the family Poaceae. In some embodiments, the transcriptional control sequence of the present invention is derived from a cereal crop plant species.

In some embodiments, the transcriptional control sequence is derived from a *Triticum* species (for example *T. aestivum, T. durum, T. monococcum, T. dicoccon, T. spelta* or *T. polonicum*). In some embodiments, the transcriptional control sequence is derived from a tetraploid wheat (for example *T. durum, T dicoccon,* or *T. polonicum*). In some embodiments, the transcriptional control sequence is derived from a durum wheat, and in some embodiments, the transcriptional control sequence is derived from *Triticum durum*.

In some embodiments, the transcriptional control sequence is derived from a gene which comprises an open reading frame comprising the nucleotide sequence set forth in SEQ ID NO: 2, or a homolog thereof.

One example of a gene which comprises an open reading frame comprising the nucleotide sequence set forth in SEQ ID NO: 2 is a gene comprising the nucleotide sequence set forth in SEQ ID NO: 4.

The term "homolog", as used herein with reference to homologs of genes comprising an open reading frame comprising the nucleotide sequence set forth in SEQ ID NO: 2, should be understood to include, for example, homologs, orthologs, paralogs, mutants and variants of genes comprising an open reading frame which comprises the nucleotide sequence set forth in SEQ ID NO: 2. In some embodiments, the homolog, ortholog, paralog, mutant or variant of a polypeptide comprising an open reading frame which comprises the nucleotide sequence set forth in SEQ ID NO: 2 comprises a nucleotide sequence which comprises at least 35% sequence identity, at least 40% sequence identity, at least 45% sequence identity, at least 50% sequence identity, at least 55% sequence identity, at least 60% sequence identity, at least 65% sequence identity, at least 70% sequence identity, at least 75% sequence identity, at least 80% sequence identity, at least 85% sequence identity, at least 90% sequence identity or at least 95% sequence identity to the nucleotide sequence set forth in SEQ ID NO: 2.

When comparing nucleotide sequences to calculate a percentage identity, the compared sequences should be compared over a comparison window of at least 500 nucleotide residues, at least 1000 nucleotide residues, at least 1500 nucleotide residues, at least 2000 nucleotide residues, at least 2500 nucleotide residues or over the full length of SEQ ID NO: 2. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerised implementations of algorithms such the BLAST family of programs as, for example, disclosed by Altschul et al., 1997 *Nucl. Acids Res.* 25: 3389-3402. A detailed discussion of sequence analysis can be found in Unit 19.3 of Ausubel et al., *Current Protocols in Molecular Biology*, John Wiley & Sons Inc, 1994-1998, Chapter 15, 1998.

In some embodiments, a homolog of a gene comprising an open reading frame comprising the nucleotide sequence set forth in SEQ ID NO: 2 may include a gene comprising an open reading frame comprising the nucleotide set forth in SEQ ID NO: 7.

In some embodiments, a homolog of a gene comprising an open reading frame comprising the nucleotide sequence set forth in SEQ ID NO: 2 may include a gene comprising an open reading frame comprising the nucleotide sequence set forth in SEQ ID NO: 17.

In some embodiments, the transcriptional control sequence contemplated by the first aspect of the invention comprises the nucleotide sequence set forth in SEQ ID NO: 3 or a functionally active fragment or variant thereof.

As set out above, the present invention also contemplates "functionally active fragments or variants" of the transcriptional control sequence of the present invention, including (but not limited to) functionally active fragments or variants of a transcriptional control sequence comprising the nucleotide sequence set forth in SEQ ID NO: 3.

"Functionally active fragments" of the transcriptional control sequence of the invention include fragments of a transcriptional control sequence which retain the capability to specifically or preferentially direct expression of an operably connected nucleotide sequence in a plant seed (or a particular cell or tissue type thereof as hereinbefore described) in at least one plant type. In some embodiments of the invention the functionally active fragment is at least 200 nucleotides (nt), at least 500 nt, at least 1000 nt, at least 1500 nt, at least 2000 nt or at least 2500 nt in length. In further embodiments, the fragment comprises at least 200 nt, at least 500 nt, at least 1000 nt, at least 1500 nt, at least 2000 nt or at least 2500 nt contiguous bases from the nucleotide sequence set forth in SEQ ID NO: 3.

"Functionally active variants" of the transcriptional control sequence of the invention include orthologs, mutants, synthetic variants, analogs and the like which are capable of effecting transcriptional control of an operably connected nucleotide sequence in a plant seed (or a particular cell or tissue type thereof as hereinbefore described) in at least one plant type. The term "variant" should be considered to specifically include, for example, orthologous transcriptional control sequences from other organisms; mutants of the transcriptional control sequence; variants of the transcriptional control sequence wherein one or more of the nucleotides within the sequence has been substituted, added or deleted; and analogs that contain one or more modified bases or DNA or RNA backbones modified for stability or for other reasons. "Modified" bases include, for example, tritylated bases and unusual bases such as inosine.

In some embodiments, the functionally active fragment or variant comprises at least 50%, at least 55%, at least 60%, at least 65%, at least 70%, at least 75%, at least 80%, at least 82%, at least 85%, at least 87%, at least 90%, at least 92%, at least 95%, at least 96%, at least 97%, at least 98% or at least 99% nucleotide sequence identity to the nucleotide sequence set forth in SEQ ID NO: 3.

When comparing nucleic acid sequences to calculate a percentage identity, the compared nucleotide sequences should be compared over a comparison window of at least 500 nucleotide residues, at least 1000 nucleotide residues, at least 1500 nucleotide residues, at least 2000 nucleotide residues, at least 2500 nucleotide residues, or over the full length of SEQ ID NO: 3. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerised implementations of algorithms such the BLAST family of programs as, for example, disclosed by Altschul et al., 1997, supra. A detailed discussion of sequence analysis can be found in Unit 19.3 of Ausubel et al., 1998, supra.

In some embodiments, the functionally active fragment or variant comprises a nucleic acid molecule which hybridises to a nucleic acid molecule defining a transcriptional control sequence of the present invention under stringent conditions. In some embodiments, the functionally active fragment or variant comprises a nucleic acid molecule which hybridises to a nucleic acid molecule comprising the nucleotide sequence set forth in SEQ ID NO: 3 under stringent conditions.

As used herein, "stringent" hybridisation conditions will be those in which the salt concentration is less than about 1.5 M Na ion, typically about 0.01 to 1.0 M Na ion concentration (or other salts) at pH 7.0 to 8.3 and the temperature is at least 30° C. Stringent conditions may also be achieved with the addition of destabilising agents such as formamide. In some embodiments, stringent hybridisation conditions may be low stringency conditions, medium stringency conditions or high stringency conditions. Exemplary low stringency conditions include hybridisation with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridisation in 40 to 45% formamide, 1.0 M NaCl, 1% SDS at 37° C., and a wash in 0.5× to 1×SSC at 55 to 60° C. Exemplary high stringency conditions include hybridisation in 50% formamide, 1 M NaCl, 1% SDS at 37° C., and a wash in 0.1×SSC at 60 to 65° C. Optionally, wash buffers may comprise about 0.1% to about 1% SDS. Duration of hybridisation is generally less than 24 hours, usually 4 to 12 hours.

Specificity of hybridisation is also a function of post-hybridisation washes, with the critical factors being the ionic strength and temperature of the final wash solution. For DNA-DNA hybrids, the $T_m$ can be approximated from the equation of Meinkoth and Wahl, 1984 *Anal. Biochem.* 138: 267-284, i.e. $T_m$=81.5° C.+16.6 (log M)+0.41 (% GC)-0.61 (% form)-500/L; where M is the molarity of monovalent cations, % GC is the percentage of guanosine and cytosine nucleotides in the DNA, % form is the percentage of formamide in the hybridisation solution, and L is the length of the hybrid in base pairs. The $T_m$ is the temperature (under defined ionic strength and pH) at which 50% of a complementary target sequence hybridises to a perfectly matched probe. $T_m$ is reduced by about 1° C. for each 1% of mismatching; thus, $T_m$, hybridisation, and/or wash conditions can be adjusted to hybridise to sequences of different degrees of complementarity. For example, sequences with ≥90% identity can be hybridised by decreasing the $T_m$ by about 10° C. Generally, stringent conditions are selected to be about 5° C. lower than the thermal melting point ($T_m$) for the specific sequence and its complement at a defined ionic strength and pH. However, high stringency conditions can utilise a hybridisation and/or wash at, for example, 1, 2, 3, or 4° C. lower than the thermal melting point ($T_m$); medium stringency conditions can utilise a hybridisation and/or wash at, for example, 6, 7, 8, 9, or 10° C. lower than the thermal melting point ($T_m$); low stringency conditions can utilise a hybridisation and/or wash at, for example, 11, 12, 13, 14, 15, or 20° C. lower than the thermal melting point ($T_m$). Using the equation, hybridisation and wash compositions, and desired $T_m$, those of ordinary skill will understand that variations in the stringency of hybridisation and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridisation of nucleic acids is found in Tijssen, *Laboratory Techniques in Biochemistry and Molecular Biology-Hybridisation with Nucleic Acid Probes*, Pt I, Chapter 2, Elsevier, N.Y., 1993; Ausubel et al., eds *Current Protocols in Molecular Biology*, Chapter 2, Greene Publishing and Wiley-Interscience, New York, 1995; and Sambrook et al., *Molecular Cloning: A Laboratory Manual*, $2^{nd}$ ed., Cold Spring Harbor Laboratory Press, Plainview, N.Y., 1989.

In some embodiments, the functionally active fragment or variant comprises one or more nucleotide sequence motifs selected from the list consisting of:

```
a prolamin box,
TGCAAAG;           (SEQ ID NO: 8)

an RY repeat motif,
CATGCATG;          (SEQ ID NO: 9)

a bZIP transcription factor binding site,
ACACNNG;           (SEQ ID NO: 10)

an E-box,
CANNTG;            (SEQ ID NO: 11)

an S-box,
CACCTCCA           (SEQ ID NO: 12)

an A-box or G motif,
TACGTA;            (SEQ ID NO: 13)
and/or a pyrimidin box,
CCTTTT.            (SEQ ID NO: 14)
```

In some embodiments, the functionally active fragment or variant comprises one or more repeats of each of the nucleotide sequence motifs noted above.

In a second aspect, the present invention also provides a nucleic acid construct comprising an isolated nucleic acid according to the first aspect of the invention.

The nucleic acid construct of the second aspect of the present invention may comprise any polyribonucleotide or polydeoxyribonucleotide, which may be unmodified RNA or DNA or modified RNA or DNA. For example, the nucleic acid construct of the invention may comprise single- and/or double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the nucleic acid construct may comprise triple-stranded regions comprising RNA or DNA or both RNA and DNA. The nucleic acid construct may also comprise one or more modified bases or DNA or RNA backbones modified for stability or for other reasons. "Modified" bases include, for example, tritylated bases and unusual bases such as inosine. A variety of modifications can be made to DNA and RNA; thus the term "nucleic acid construct" embraces chemically, enzymatically, or metabolically modified forms.

In some embodiments, the nucleic acid construct comprises DNA. Accordingly, the nucleic acid construct of the present invention may comprise, for example, a linear DNA molecule, a plasmid, a transposon, a cosmid, an artificial chromosome or the like. Furthermore, the nucleic acid construct of the present invention may be a separate nucleic acid molecule or may be a part of a larger nucleic acid molecule.

In some embodiments, the nucleic acid construct further comprises a nucleotide sequence of interest operably connected to the transcriptional control sequence, or functionally active fragment or variant thereof, according to the first aspect of the invention.

In some embodiments the nucleotide sequence of interest is heterologous with respect to the transcriptional control sequence, or functionally active fragment or variant thereof, according to the first aspect of the invention.

The term "heterologous with respect to the transcriptional control sequence" refers to the nucleotide sequence of interest being any nucleotide sequence other than that which the transcriptional control sequence (or functionally active fragment or variant thereof) is operably connected to in its natural state. For example, in its natural state, SEQ ID NO: 3 is operably connected to the nucleotide sequence set forth in SEQ ID NO: 4. Accordingly, in this example, any nucleotide sequence other than a nucleotide sequence consisting of the nucleotide sequence set forth in SEQ ID NO: 4 should be considered heterologous with respect to SEQ ID NO: 3.

In accordance with the definition above, it would be recognised that a nucleotide sequence of interest which is heterologous to a transcriptional control sequence (or functionally active fragment or variant thereof) may be derived from an organism of a different taxon to the transcriptional control sequence (or functionally active fragment or variant thereof) or the nucleotide sequence of interest may be a heterologous sequence from an organism of the same taxon.

In some embodiments, the nucleic acid construct may further comprise a nucleotide sequence defining a transcription terminator. The term "transcription terminator" or "terminator" refers to a DNA sequence at the end of a transcriptional unit which signals termination of transcription. Terminators are generally 3'-non-translated DNA sequences and may contain a polyadenylation signal, which facilitates the addition of polyadenylate sequences to the 3'-end of a primary transcript. As with promoter sequences, the terminator may be any terminator sequence which is operable in the cells, tissues or organs in which it is intended to be used. Examples of suitable terminator sequences which may be useful in plant cells include: the nopaline synthase (nos) terminator, the CaMV $^{35}$S terminator, the octopine synthase (ocs) terminator, potato proteinase inhibitor gene (pin) terminators, such as the pinII and pinIII terminators and the like.

In some embodiments the nucleic acid construct comprises an expression cassette comprising the structure:

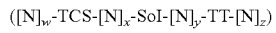

wherein:

[N]<sub>w</sub> comprises one or more nucleotide residues, or is absent;

TCS comprises a nucleic acid according to the first aspect of the invention;

[N]<sub>x</sub> comprises one or more nucleotide residues, or is absent;

SoI comprises a nucleotide sequence of interest which is operably connected to the TCS;

[N]<sub>y</sub> comprises one or more nucleotide residues, or is absent;

TT comprises a nucleotide sequence defining a transcription terminator;

[N]<sub>z</sub> comprises one or more nucleotide residues, or is absent.

The nucleic acid construct of the present invention may further comprise other nucleotide sequences as desired. For example, the nucleic acid construct may include an origin of replication for one or more hosts, a selectable marker gene which is active in one or more hosts, or the like.

As used herein, the term "selectable marker gene" includes any gene that confers a phenotype on a cell, in which it is expressed, to facilitate the identification and/or selection of cells which are transformed with a nucleic acid construct of the invention. A range of nucleotide sequences encoding suitable selectable markers are known in the art. Exemplary nucleotide sequences that encode selectable markers include: antibiotic resistance genes such as ampicillin-resistance genes, tetracycline-resistance genes, kanamycin-resistance genes, the AURI-C gene which confers resistance to the antibiotic aureobasidin A, neomycin phosphotransferase genes (e.g. nptI and nptII) and hygromycin phosphotransferase genes (e.g. hpt); herbicide resistance genes including glufosinate, phosphinothricin or bialaphos resistance genes such as phosphinothricin acetyl transferase-encoding genes (e.g. bar), glyphosate resistance genes including 3-enoyl pyruvyl shikimate 5-phosphate synthase-encoding genes (e.g. aroA), bromyxnil resistance genes including bromyxnil nitrilase-encoding genes, sulfonamide resistance genes including dihydropterate synthase-encoding genes (e.g. sul) and sulfonylurea resistance genes including acetolactate synthase-encoding genes; enzyme-encoding reporter genes such as GUS-encoding and chloramphenicolacetyltransferase (CAT)-encoding genes; fluorescent reporter genes such as the green fluorescent protein-encoding gene; and luminescence-based reporter genes such as the luciferase gene, amongst others.

The constructs described herein may further include nucleotide sequences intended for the maintenance and/or replication of the construct in prokaryotes or eukaryotes and/or the integration of the construct or a part thereof into the genome of a eukaryotic or prokaryotic cell.

In some embodiments, the construct according to the second aspect of the invention is adapted to be at least partially transferred into a plant cell via *Agrobacterium*-mediated transformation. Accordingly, in some embodiments, the nucleic acid construct may comprise left and/or right T-DNA border sequences. Suitable T-DNA border sequences would be readily ascertained by one of skill in the art. However, the term "T-DNA border sequences" should be understood to at least include, for example, any substantially homologous and substantially directly repeated nucleotide sequences that delimit a nucleic acid molecule that is transferred from an *Agrobacterium* sp. cell into a plant cell susceptible to *Agrobacterium*-mediated transformation. By way of example, reference is made to the paper of Peralta and Ream, 1985, *Proc.* *Natl. Acad. Sci. USA,* 82(15): 5112-5116, and the review of Gelvin, 2003, *Microbiology and Molecular Biology Reviews,* 67(1): 16-37.

In some embodiments, the present invention also contemplates any suitable modifications to the construct which facilitate bacterial mediated insertion into a plant cell via bacteria other than *Agrobacterium* sp., for example, as described in Broothaerts et al., 2005, *Nature* 433: 629-633.

In some embodiments, the construct according to the second aspect of the invention may also comprise nucleotide sequences that encode regulatory microRNAs ("miRNA") and/or a target sequence for a miRNA, which may further modulate the expression pattern determined by the nucleotide sequence of the first aspect of the invention. A discussion of the regulatory activity of microRNAs in plants may be found in the review of Jones-Rhoades et al., 2006, *Annual Review of Plant Biology* 57: 19-53.

Those skilled in the art will be aware of how to produce the constructs described herein, and of the requirements for obtaining the expression thereof, when so desired, in a specific cell or cell-type under the conditions desired. In particular, it will be known to those skilled in the art that the genetic manipulations required to perform the present invention may require the propagation of a construct described herein or a derivative thereof in a prokaryotic cell such as an *E. coli* cell or a plant cell or an animal cell. Exemplary methods for cloning nucleic acid molecules are described in Sambrook et al., *Molecular Cloning: A Laboratory Manual*, Cold Spring Harbor Laboratory Press, New York, 2000.

In a third aspect, the present invention provides a cell comprising a nucleic acid construct according to the second aspect of the invention.

The nucleic acid construct may be maintained in the cell as a nucleic acid molecule, as an autonomously replicating genetic element (e.g. a plasmid, cosmid, artificial chromosome or the like) or it may be integrated into the genomic DNA of the cell.

As used herein, the term "genomic DNA" should be understood in its broadest context to include any and all endogenous DNA that makes up the genetic complement of a cell. As such, the genomic DNA of a cell should be understood to include chromosomes, mitochondrial DNA, plastid DNA, chloroplast DNA, endogenous plasmid DNA and the like. As such, the term "genomically integrated" contemplates any of chromosomal integration, mitochondrial DNA integration, plastid DNA integration, chloroplast DNA integration, endogenous plasmid integration, or the like. A "genomically integrated form" of the construct may be all or part of the construct. However, in some embodiments the genomically integrated form of the construct at least includes the nucleic acid molecule of the first aspect of the invention.

The cells contemplated by the third aspect of the invention include any prokaryotic or eukaryotic cell. In some embodiments, the cell is a plant cell. In some embodiments the cell is a monocotyledonous plant cell. In some embodiments the cell is a cell from a plant in the family Poaceae. In some embodiments the cell is a cereal crop plant cell. In some embodiments the cell is a wheat cell, a barley cell or a rice cell.

In some embodiments, the cell may also comprise a prokaryotic cell. For example, the prokaryotic cell may include an *Agrobacterium* sp. cell (or other bacterial cell), which carries the nucleic acid construct and which may, for example, be used to transform a plant. In some embodiments, the prokaryotic cell may be a cell used in the construction or cloning of the nucleic acid construct (e.g. an *E. coli* cell).

In a fourth aspect, the present invention provides a multicellular structure comprising one or more cells according to the third aspect of the invention.

In some embodiments, the multicellular structure comprises a plant or a part, organ or tissue thereof. As referred to herein, "a plant or a part, organ or tissue thereof" should be understood to specifically include a whole plant; a plant tissue; a plant organ; a plant part; a plant embryo; and cultured plant tissue such as a callus or suspension culture.

In some embodiments of the fourth aspect of the invention, the plant or part, organ or tissue thereof comprises reproductive material for a plant including, for example, seeds, flowers, vegetative plant material, explants, plant tissue in culture including callus or suspension culture and the like.

As would be appreciated from the remainder of the specification the plant or a part, organ or tissue thereof contemplated in the fourth aspect of the invention may include, for example, any of a monocot, a plant in the family Poaceae, a cereal crop plant, a wheat plant, a barley plant, or a rice plant or a part, organ or tissue of any of the foregoing.

In some embodiments of the fourth aspect of the invention, the plant or part, organ or tissue thereof comprises a seed as hereinbefore defined.

In some embodiments of the fourth aspect of the invention, a nucleotide sequence of interest may be operably connected to the transcriptional control sequence, or a functionally active fragment or variant thereof, such that the nucleotide sequence of interest is specifically or preferentially expressed in a seed, or in a particular cell or tissue type thereof, and optionally at a particular developmental stage, as described above with respect to the first aspect of the invention.

In a fifth aspect, the present invention provides a method for specifically or preferentially expressing a nucleotide sequence of interest in one or more parts of a plant seed, the method comprising effecting transcription of the nucleotide sequence of interest in a plant under the transcriptional control of a nucleic acid according to the first aspect of the invention.

As set out above, in its fifth aspect, the present invention is predicated, in part, on effecting transcription of the nucleotide sequence of interest under the transcriptional control of a transcriptional control sequence of the first aspect of the invention. In some embodiments, this is effected by introducing a nucleic acid molecule comprising the transcriptional control sequence, or a functionally active fragment or variant thereof, into a cell of the plant, such that the nucleotide sequence of interest is operably connected to the transcriptional control sequence. The nucleic acid molecule may be introduced into the plant via any method known in the art. For example, an explant or cultured plant tissue may be transformed with a nucleic acid molecule, wherein the explant or cultured plant tissue is subsequently regenerated into a mature plant including the nucleic acid molecule; a nucleic acid may be directly transformed into a plant, either stably or transiently; a nucleic acid may be introduced into a plant via plant breeding using a parent plant that carries the nucleic acid molecule; and the like.

In some embodiments, the nucleic acid molecule is introduced into a plant cell via transformation. Plants may be transformed using any method known in the art that is appropriate for the particular plant species. Common methods include *Agrobacterium*-mediated transformation, microprojectile bombardment based transformation methods and direct DNA uptake based methods. Roa-Rodriguez et al., *Agrobacterium*-mediated transformation of plants, 3$^{rd}$ Ed. CAMBIA Intellectual Property Resource, Canberra, Australia, 2003, review a wide array of suitable *Agrobacterium*-mediated plant transformation methods for a wide range of plant species. Other bacterial-mediated plant transformation methods may also be utilised, for example, see Broothaerts et al., 2005, supra Microprojectile bombardment may also be used to transform plant tissue and methods for the transformation of plants, particularly cereal plants, reviewed by Casas et al., 1995, *Plant Breeding Rev.* 13: 235-264 Direct DNA uptake transformation protocols such as protoplast transformation and electroporation are described in detail in Galbraith et al., (eds.), *Methods in Cell Biology Vol.* 50, Academic Press, San Diego, 1995. In addition to the methods mentioned above, a range of other transformation protocols may also be used. These include infiltration, electroporation of cells and tissues, electroporation of embryos, microinjection, pollen-tube pathway-, silicon carbide- and liposome mediated transformation. Methods such as these are reviewed by Rakoczy-Trojanowska, 2002, *Cell. Mol. Biol. Lett.* 7: 849-858. A range of other plant transformation methods may also be evident to those of skill in the art and, accordingly, the present invention should not be considered in any way limited to the particular plant transformation methods exemplified above.

As set out above, the transcriptional control sequence of the present invention is introduced into a plant cell such that the nucleotide sequence of interest is operably connected to the transcriptional control sequence and the present invention contemplates any method to effect this. For example, the subject transcriptional control sequence and a nucleotide sequence of interest may be incorporated into a nucleic acid molecule such that they are operably connected, and this construct may be introduced into the target cell. In another example, the nucleic acid sequence of the present invention may be inserted into the genome of a target cell such that it is placed in operable connection with an endogenous nucleic acid sequence. As would be recognised by one of skill in the art, the insertion of the transcriptional control sequence into the genome of a target cell may be either by non-site specific insertion using standard transformation vectors and protocols or by site-specific insertion, for example, as described in Terada et al., 2002, *Nat Biotechnol* 20: 1030-1034.

The nucleotide sequence of interest, which is placed under the regulatory control of the transcriptional control sequence of the present invention, may be any nucleotide sequence of interest. General categories of nucleotide sequences of interest include nucleotide sequences which encode, for example: reporter proteins, such as, GUS, GFP and the like; proteins involved in cellular metabolism such as Zinc finger proteins, kinases, heat shock proteins and the like; proteins involved in agronomic traits such as disease or pest resistance or herbicide resistance; proteins involved in grain characteristics such as grain biomass, nutritional value, post-harvest characteristics and the like; heterologous proteins, such as proteins encoding heterologous enzymes or structural proteins or proteins involved in biosynthetic pathways for heterologous products; "terminator" associated proteins such as barnase, barstar or diphtheria toxin. Furthermore, the nucleotide sequence of interest may alternatively encode a non-translated RNA, for example an siRNA, miRNA, antisense RNA and the like.

In some embodiments, the nucleotide sequence of interest may comprise, for example, a pathogen responsive (PR) gene, a resistance (R) gene or a defensin gene. In some embodiments, the nucleotide sequence of interest may encode a protein such as PDR5 or TRI101. Such proteins may be expressed in a seed-specific manner in crop plants, such as wheat, in order to lower the incidence of diseases such as head blight (caused by *Fusarium graminearum* or *Gibberella zeae*) and/or reduce mycotoxin levels within the seed.

The method according to the fifth aspect of the present invention may be applicable to effect specific or preferential expression of a nucleotide sequence of interest in a range of different plant seeds. For example, in some embodiments, the plant may be a monocotyledonous plant. In some embodiments, the plant may be a plant in the family Poaceae. In some embodiments, the plant may be a cereal crop plant. In some embodiments the method according to the fifth aspect of the present invention may be applicable to effect specific or preferential expression of a nucleotide sequence of interest in the seed of a wheat plant, a barley plant and/or a rice plant.

As set out above, the method according to the fifth aspect of the present invention may also be used to specifically or preferentially direct expression of a nucleotide sequence of interest in a particular cell or tissue of a plant seed and/or specifically or preferentially direct expression at a particular developmental stage of a plant seed.

In some embodiments, the transcriptional control sequence directs expression of an operably connected nucleotide sequence in the embyro, or a part thereof, in the seed.

In some embodiments, the transcriptional control sequence directs expression of an operably connected nucleotide sequence in the endosperm, or a part thereof, in the seed.

In further embodiments of the method according to the fifth aspect of the invention, the nucleotide sequence of interest is heterologous with respect to the transcriptional control sequence, as defined supra.

Finally, reference is made to standard textbooks of molecular biology that contain methods for carrying out basic techniques encompassed by the present invention, including DNA restriction and ligation for the generation of the various constructs described herein. See, for example, Maniatis et al., *Molecular Cloning: A Laboratory Manual*, Cold Spring Harbor Laboratory Press, New York, 1982 and Sambrook et al., 2000, supra.

The present invention is further described by the following non-limiting examples. It is to be understood that the following description is for the purpose of describing particular embodiments only and is not intended to be limiting with respect to the above description.

EXAMPLE 1

Cloning of the TdGL9L Gene

The full length cDNA of TaGL9 was isolated from a Y2H cDNA library prepared from the whole grain of *Triticum aestivum*, cultivar Chinese Spring at 0-6 DAP. The library was screened with a bait DNA sequence, which included a 4× tandem repeat of the cis-element, CATTAAATG (SEQ ID NO: 15), which is known to be specific for homeodomain/leucine zipper class IV (HDZipIV) transcription factors (TFs).

Seven of forty eight analysed positive clones were grouped as two and five clones with inserts 2.6 and 3.3 kb, respectively. Sequencing revealed that inserts encoded two different cDNAs containing full length coding regions of HDZipIV TFs. One of them, designated GLABRA2 like clone 9 from wheat (TaGL9), was 2.6 kb long (SEQ ID NO: 7).

A database search using the deduced TaGL9 protein sequence (SEQ ID NO: 6) revealed 46.2% identity to the sequence of protein product of the closest annotated homologue OSTF1 (GenBank accession number AF317882).

Southern blot hybridisation of nullisomic-tetrasomic lines of hexaploid wheat with the 3' UTR of TaGL9 as a probe revealed that TaGL9 is located on group 3 chromosomes of hexaploid wheat.

A 172 bp long fragment of the 3' untranslated region (3'UTR) of TaGL9 was used as a probe to screen a bacterial artificial chromosome (BAC) library prepared from genomic DNA of *Triticum. durum* cv. Langdon. Using Southern hybridisation, five BAC clones were identified and three were selected for further analysis on the basis of the strength of the hybridisation signals.

DNA from the three selected BAC clones was isolated and used as a template for PCR with primers derived from the coding region and 3'UTR of TaGL9. One BAC clone gave a PCR product. Sequencing of this BAC clone revealed that the cloned insert contained a close homologue/homeologue of TaGL9 from *T. durum*, which was designated TdGL9L (SEQ ID NO: 4), also referred to herein as TdGL9H1. The TdGL9L cDNA sequence was designated SEQ ID NO: 2. The coding region of the cloned gene was found to be interrupted with 10 introns.

The full coding region of the second identified cDNA, designated TdGL9H2, was isolated from a cDNA pool prepared from developing seed of T. durum. Primers for the nested RT-PCR were derived from the genomic sequence of TdGL9L (TdGL9H1).

The deduced protein sequences of TdGL9L (SEQ ID NO: 1) and TdGL9H2 (SEQ ID NO: 16) have 83.0% and 80.9% identity, respectively, with TaGL9, and 46.5% and 46.8% identity, respectively, with OsTF1. The protein sequence of TdGL9L has 91.4% identity to TdGL9H2.

Phylogenetic relationships based on the amino acid sequences of TaGL9, TdGL9L, (TdGL9H1), and TdGL9H2, and the sequences of the HDZip class IV proteins from other plant species annotated so far in NCBI databases, are shown in FIG. 1A. The closest homologue of the identified GL9 proteins is OsTF1.

An alignment of TaGL9 to protein sequences of TdGL9L (TdGL9H1), TdGL9H2 and OsTF1 is shown in FIG. 1B. The closest homologues of GL9 proteins from *Arabidopsis*, AtHDG8, AtHDG9, AtHDG10 and FWA/AtHDG6, share about 30% amino acid sequence identity with wheat GL9 proteins.

As can be seen from the phylogenetic tree using protein sequences from members of class IV HDZip transcription factors from different plants, TaGL9, TdGL9L and TdGL9H2 proteins are relatively divergent from most other members of the class IV HDZip family.

EXAMPLE 2

Sequence Analysis of the TdGL9L Promoter

Computer analysis of the 3029 bp long TdGL9L promoter (SEQ ID NO: 3) revealed a large number of cis-elements which are associated with specific gene expression in the endosperm, embryo and seeds.

The TdGL9L promoter contains a prolamin box, TGCAAAG (SEQ ID NO: 8). The prolamin box is known to be involved in the quantitative regulation of endosperm specific genes. Another quantitative element identified in the TdGL9L promoter is the RY repeat motif, CATGCATG (SEQ ID NO: 9), which is responsible for the seed specific expression of many genes of both dicotyledonous and monocotyledonous plants. In addition, the binding site for embryo specific bZIP transcription factors, ACACNNG (SEQ ID NO: 10) is repeated 8 times in the TdGL9L promoter. The promoter also contains multiple E-boxes, CANNTG (SEQ ID NO: 11) which usually act together with ABRE elements and are responsible for seed specific expression.

In addition to the seed specific cis-elements noted above, the TdGL9L promoter is enriched for sugar responsive elements. One of the identified elements is the S-box, CACCTCCA (SEQ ID NO: 12), which was found earlier to be conserved in several rbcS promoters in *Arabidopsis*. The promoter also contains an A-box or G motif, TACGTA (SEQ ID NO: 13), which is a binding site for bZIP factors responsible for sugar repression. The pyrimidin box, CCTTTT (SEQ ID NO: 14) that was reported to be partially responsible for sugar mediated repression is also repeated 4 times in the TdGL9L promoter.

EXAMPLE 3

Spatial and Temporal Patterns of TaGL9 and TdGL9L (TdGL9H1) Expression

Figure 2:
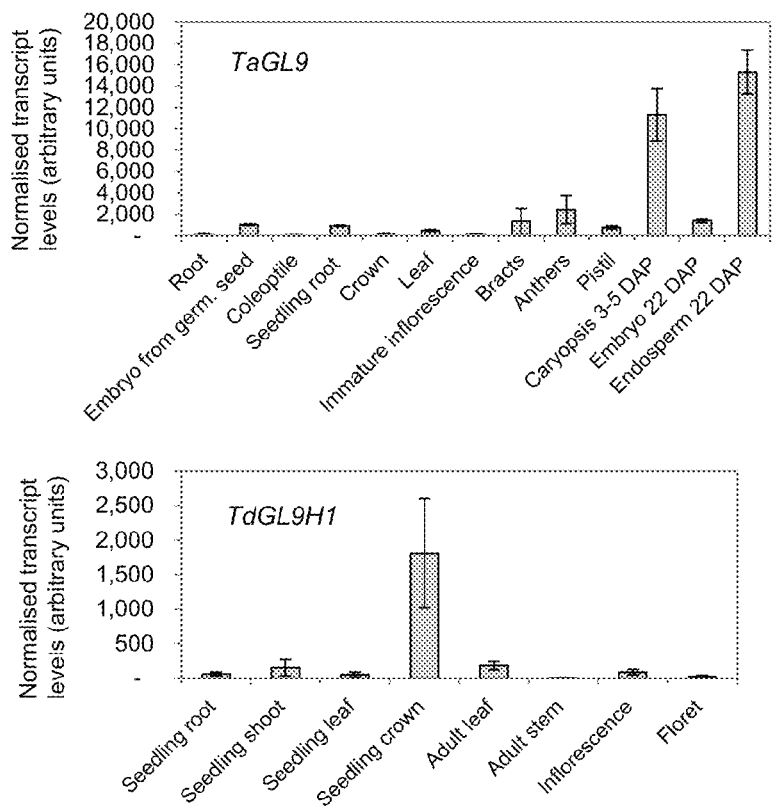
FIG. 2 shows graphs of Q-PCR analysis of TaGL9 and TdGL9L (TdGL9H1) expression. (A) Expression of TaGL9 (upper panel) and TdGL9L (lower panel) in different wheat tissues; (B) Expression of TaGL9 (upper panel) and TdGL9L (lower panel) in developing wheat grain at defined DAP.
Figure 2:
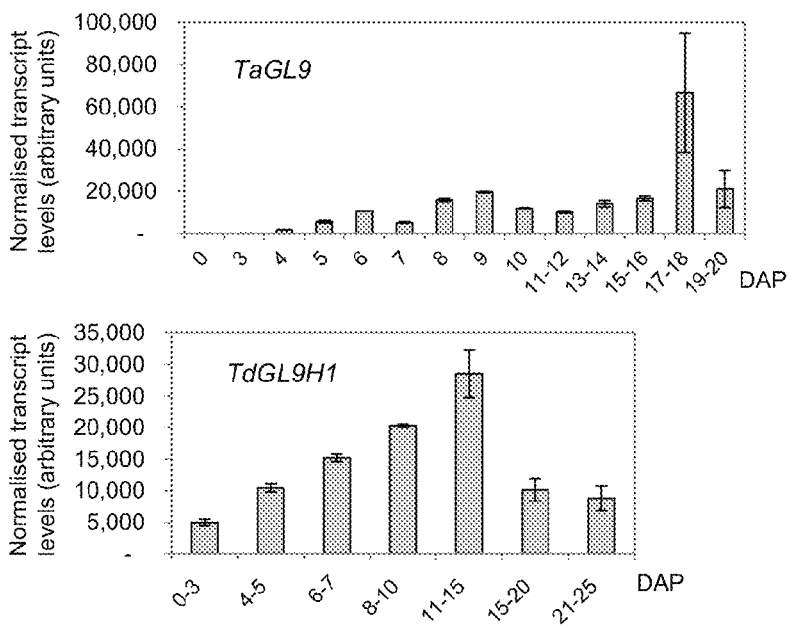

Expression of TaGL9 and TdGL9L (TdGL9H1) in different wheat (*T. aestivum* cv. Chinese Spring and *T. durum* cv. Langdon, respectively) tissues was analysed using Q-PCR. TaGL9 was found to be weakly expressed in anthers, mature embryos at 22 DAP, and in the embryo and roots of germinating seedlings. Strong expression was detected in the caryopsis at 3-5 DAP and endosperm at 22 DAP (FIG. 2A, upper panel). Expression of TaGL9 in grain was detected at 4 DAP and was observed until 20 DAP. It decreased at 7 DAP (coinciding with filling of endosperm with starch), but later increased again to peak at 17-18 DAP (FIG. 2B, upper panel). No expression of TdGL9L (TdGL9H1) was detected in all tested tissues except low level of expression in crown (FIG. 2A, lower panel). In grain, expression of TdGL9L (TdGL9H1) constantly increased, reached maximum at 11-15 DAP, and then began to decrease (FIG. 2B, lower panel).

EXAMPLE 4

Activity of the Wheat TdGL9L Promoter in the Developing and Mature Grain of Wheat, Barley and Rice Spatial and temporal expression patterns of TdGL9L were examined by generating TdGL9L promoter-GUS fusion constructs and stable transformation of these constructs into wheat, barley and rice plants.

Figure 3:
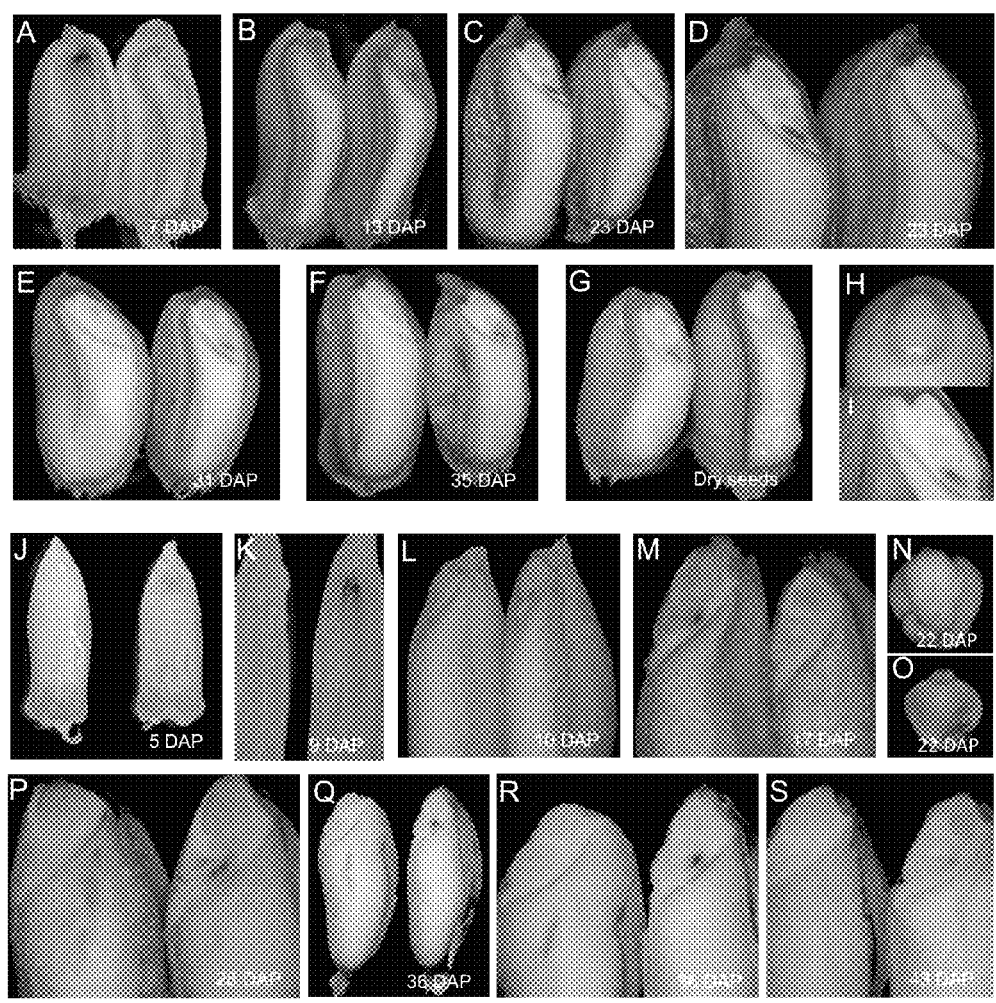
FIG. 3 shows the results of GUS expression driven by the TdGL9L (TdGL9H1) promoter in transgenic wheat (A-I) and barley (J-S) grain: uncut grain (H and J), isolated embryo (N—embryo axis side, O—scutellum side) and longitudinal hand-cuts (the rest of pictures). Control grain of the same age is shown on the right (A, C, D, G and M) and left (the rest of pictures) side of each picture. Stage of grain development in days after pollination (DAP) is shown in lower right corner of each picture. $T_1$ grain from Line 19, 3 weeks after the harvest (G, H and I); $T_2$ grain from sublines of Line 19 (A and C—H); $T_2$ grain from sublines of Line 4 (B and I); $T_2$ grain from sublines of Line 14 (J-S).
Figure 4:
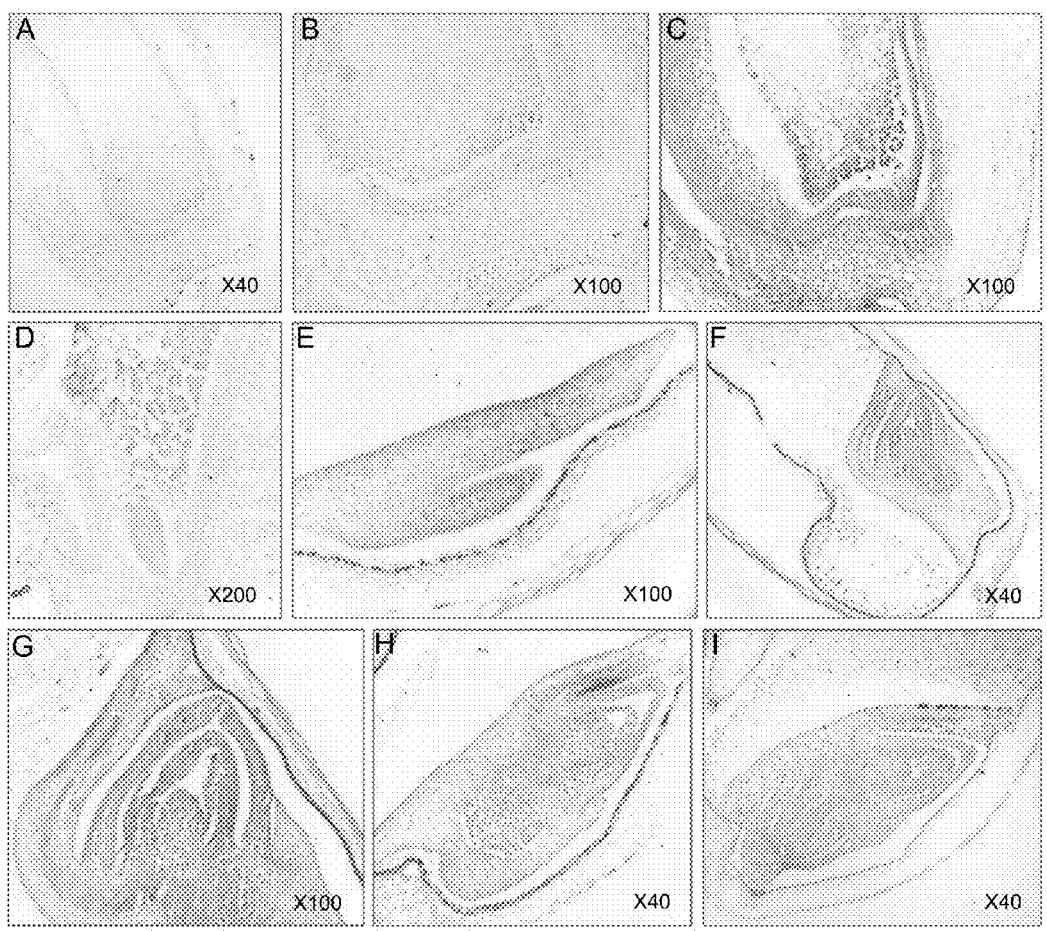
FIG. 4 shows activity of the TdGL9L (TdGL9H1) promoter in transgenic wheat grain detected using histological GUS assay. Promoter active in the portion of endosperm surrounding embryo at 6 (A-C) and 8 (D) DAP; GUS staining detected in the main vascular bundle of the scutellum at 13 (E), 18 (F and G), 23 (H) and 35 (I) DAP. $T_2$ grain from the subline of Line 4 (E); the rest of pictures—$T_2$ grain from different sublines of Line 19; em—embryo, en—endosperm; magnification is shown in the lower right corner of each picture. Grain samples were counterstained with Safranin O.
Figure 5:
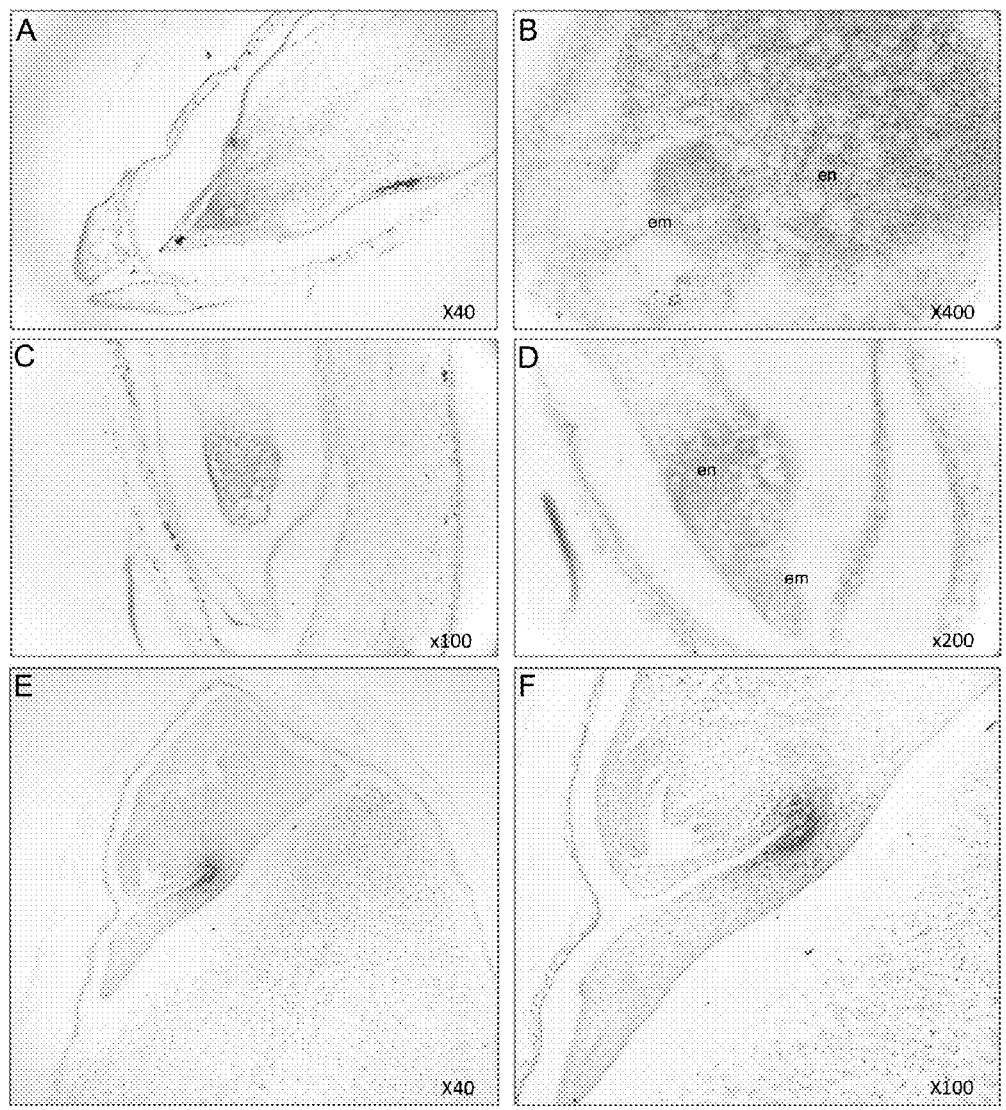
FIG. 5 shows activity of the TdGL9L (TdGL9H1) promoter in transgenic barley grain detected using histological GUS assay. Promoter active in the portion of endosperm surrounding embryo at 5 DAP (A-D); GUS staining detected in the main vascular bundle of the scutellum at 16 DAP (E and F). $T_1$ grain from Line 14 (A, B, E and F); $T_2$ grain from subline of Line 4 (C and D); em—embryo, en—endosperm; magnification is shown in the lower right corner of each picture. Grain samples were counterstained with Safranin O.

Whole-mount and histochemical GUS staining patterns were analyzed in independent transgenic lines. GUS staining was initially observed in wheat, barley and rice grains in areas surrounding embryos at 5 DAP. Embryos at this stage of development have a near globular shape and initiation of the primordium of the seminal root, shoot apex and vascular bundle of the scutellum has just commenced (FIGS. 3A and J; 4A-D; 5A-D). Histochemical analysis of transgenic wheat and barley grains at 5-8 DAP revealed GUS expression in the embryo and endosperm; the strongest expression was observed in the outer cell layer(s), e.g. the epidermal cell layer of the embryo and the fraction of partially cellulorised endosperm adjacent to the embryo (FIGS. 4A-D; 5A-D; 6G). No expression was detected in the rest of the endosperm.

In the developed embryo of wheat, barley and rice after 11-12 DAP, when multiplication of cells by cell division has almost ceased and development of the vascular bundle system is completed, strong activity of the promoter was detected in the main vascular bundle of the scutellum, which is responsible for the supply of nutrients (sugars) to shoots of the embryo axis (FIGS. 3B-I and M-S; 4E-I; 5E and F; 6B-F and H-L). GUS expression slowly increased in rice or remained the same in wheat and barley until grains had fully developed (FIGS. 3B-I and M-S; 6B-F). GUS activity was also detected in the main vascular bundle of the scutellum several weeks after grain was harvested (FIG. 3G-I). No GUS expression was detected in any other part of the embryo.

Figure 6:
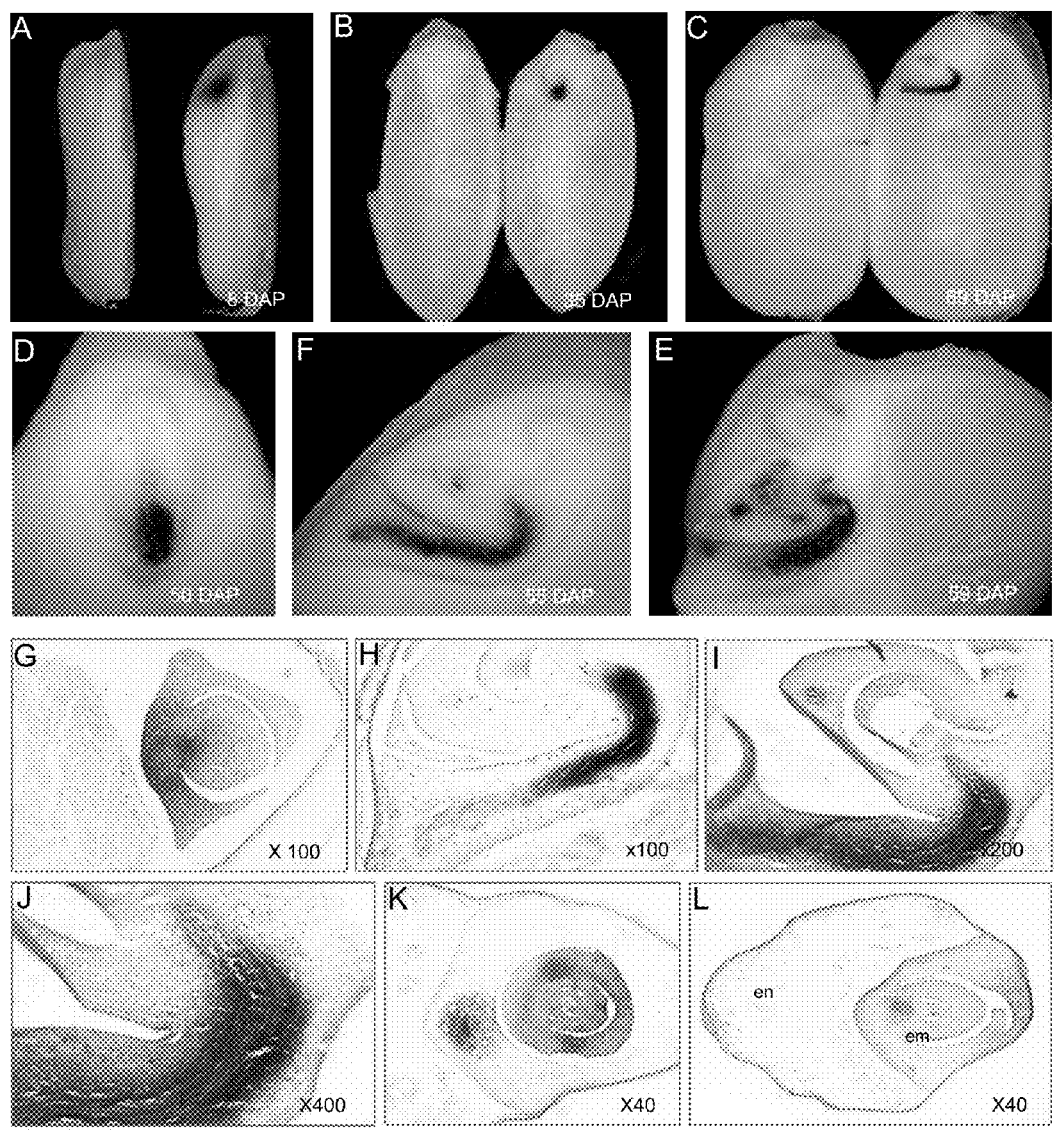
FIG. 6 shows activity of the TdGL9L (TdGL9H1) promoter in grain of transgenic rice. Longitudinal sections of rice grain at different stages of development (A-F) indicated in DAP in the lower right corner. Control grain is shown on the left side of the picture (A-C). Histological GUS assay of longitudinal grain sections (G-K) at 8 (G), 26 (H) and 69 (I-K) DAP, and section of the embryo isolated from grain at 59 DAP cut from the scutellum side (L); em—embryo, en—endosperm; magnification is shown in the lower right corner of each picture. Samples were counterstained with Safranin O.

Similarly to wheat, the activity of the TdGL9L promoter in transgenic rice plants was initially observed at 5 DAP in endosperm around the embryo (FIGS. 6A and G) and later, between 12-50 DAP, found only in the main vascular bundle of the scutellum (FIGS. 6B, D and G). However, beyond 50 DAP, GUS staining also appeared in the shoots of embryos (FIGS. 6C, E, F, H and I-L). Later, at 59 DAP, GUS expression was detected everywhere in embryonic coleoptiles and leaves, with the strongest expression in vascular bundles and adaxial parts of coleoptiles (FIGS. 6F and K). This pattern of GUS staining in transgenic rice plants did not change until at least 69 DAP (FIG. 6K) and remained in harvested grain. However, it quickly disappeared during imbibition and following germination (data not shown). No activity of the TdGL9L promoter has been detected in other tested tissues of wheat, barley and rice including leaf, stem, root, meristems, and different parts of flower (data not shown).

EXAMPLE 5

Experimental Procedures

Gene Cloning and Plasmid Construction

The full length cDNA of TaGL9 was isolated from a yeast 2-hybrid cDNA library prepared from wheat grain at 0-6 DAP using a 4× repeat of the sequence CATTAAATG (SEQ ID NO: 15) as bait according to the procedure described by Lopato et al., 2006, *Plant Methods* 2: 3-17. The 3'UTR of the cDNA sequence of TaGL9 was used as a probe to screen BAC library prepared from the genomic DNA of *Triticum durum* cv. Langdon (see Cenci et al., 2003, *Theoretical and Applied Genetics* 107(5): 931-939) using Southern blot hybridisation. Five BAC clones hybridised to the probe. DNA from three BAC clones, (#1037 G19; #1076 B10 and #1286 C15), which strongly hybridised to the probe, were isolated using a Large Construct Kit (QIAGEN). The BAC DNAs were used as templates for PCR with primers derived from the coding and 3'UTR regions of TaGL9 cDNA. One BAC clone (#1037 G19) gave a PCR product. DNA isolated from this BAC clone was sequenced using the 454 sequencing method. The obtained gene sequence was subsequently used to design forward and reverse primers for the isolation of the promoter segment.

The promoter with the full-length 5'-untranslated region was amplified by PCR using AccuPrime™ Pfx DNA polymerase (Invitrogen) from DNA of BAC clone #1037 G19 as a template. It was cloned into the pENTR-D-TOPO vector (Invitrogen); the cloned insert was verified by sequencing and subcloned into the pMDC164 vector (Curtis and Grossniklaus, 2003, *Plant Physiology* 133(2): 462-469) using recombination cloning. Selectable marker genes conferred hygromycin resistance in plants and kanamycin resistance in bacteria. The resulting binary vector designated pTdGL9L was introduced into *Agrobacterium tumefaciens* AGL1 strain by electroporation. For wheat transformation, the construct containing the TdGL9L promoter was linearised using the unique PmeI site in the vector sequence and transformed using biolistic bombardment method described by Kovalchuk et al., 2009 *Plant Molecular Biology* 71(1-2): 81-98 as described below.

Quantitative PCR (Q-PCR) Analysis

Q-PCR analysis of the expression of TaGL9 and TdGL9L (TdGL9H1) genes in different tissues of wild type wheat and at different stages of grain development was performed as described by Morran et al., 2011, *Plant Biotechnol. J.*, 9: 230-249.

Plant Transformation and Analyses

The construct pTdGL9L was transformed into barley (*Hordeum vulgare* cv. Golden Promise) using *Agrobacterium*-mediated transformation and the method developed by Tingay et al., 2001, *Plant Journal* 11(6): 1369-1376, and modified by Matthews et al., 2001, *Molecular Breeding* 7(3): 195-202.

Rice (*Oryza sativa* L. ssp. Japonica cv. Nipponbare) was transformed using the method of Sallaud et al., 2001, *Plant Journal* 39: 450-464.

Wheat (*Triticum aestivum* L. cv. Bobwhite) was transformed using biolistic bombardment as described by Kovalchuk et al., 2009, supra. Transgene integration was confirmed by PCR using GUS— specific primers.

Whole-mount and histological GUS assays were performed as described by Li et al., 2007, *Plant Biotechnol. J.* 6: 465-476, using $T_0$-$T_1$ transgenic plants and $T_1$-$T_2$ seeds, respectively.

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of the steps or features.

Also, it must be noted that, as used herein, the singular forms "a", "an" and "the" include plural aspects unless the context already dictates otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

All publications, patents, patent applications, Genbank numbers, and websites cited herein are hereby incorporated by reference in their entireties for all purposes

What is claimed is:

1. A nucleic acid construct comprising a transcription control sequence operably connected to a heterologous nucleotide sequence of interest, wherein the transcription control sequence specifically or preferentially directs expression of the operably connected heterologous nucleotide sequence of interest in one or more parts of a plant seed, and wherein said transcription control sequence comprises:
   (i) the nucleotide sequence set forth in SEQ ID NO: 3; or
   (ii) a nucleotide sequence that is at least 95% identical to SEQ ID NO: 3 and comprises the sequence motifs TGCAAAG, CATGCATG, ACACNNG, CANNTG, CACCTCCA, TACGTA and CCTTTT.

2. The nucleic acid construct of claim 1 wherein the transcription control sequence directs expression of the operably connected heterologous nucleotide sequence of interest in one or more parts of a seed of a monocotyledonous plant.

3. The nucleic acid construct of claim 2 wherein the monocotyledonous plant is a plant in the family Poaceae.

4. The nucleic acid construct of claim 1 wherein the transcription control sequence directs expression of the operably connected heterologous nucleotide sequence of interest in the embryo, or a part thereof, in the seed, or directs expression of the operably connected heterologous nucleotide sequence of interest in the endosperm, or a part thereof, in the seed.

5. A cell comprising a nucleic acid construct according to claim 1.

6. The cell of claim 5 wherein the cell is a plant cell.

7. The cell of claim 6 wherein the cell is a monocotyledonous plant cell.

8. The cell of claim 7 wherein the cell is a cell from a plant in the family Poaceae.

9. A multicellular structure comprising one or more cells according to claim 5.

10. The multicellular structure of claim 9 wherein the multicellular structure comprises a plant or a part, organ or tissue thereof.

11. The multicellular structure of claim 10 wherein the plant or a part, organ or tissue thereof, comprises a seed or a part thereof.

12. A method for specifically or preferentially expressing a nucleotide sequence of interest in one or more parts of a plant seed, the method comprising introducing the nucleic acid construct of claim 1 into a plant.

13. The method of claim 12 wherein the plant is a monocotyledonous plant.

14. The method of claim 13 wherein the plant is a plant in the family Poaceae.

15. The method of claim 12 wherein the transcription control sequence directs expression of the operably connected heterologous nucleotide sequence of interest in the embryo, or a part thereof, in the seed, or directs expression of the operably connected nucleotide sequence of interest in the endosperm, or a part thereof, in the seed.

* * * * *

SEQUENCE LISTING

<160> NUMBER OF SEQ ID NOS: 17

<210> SEQ ID NO 1
<211> LENGTH: 674
<212> TYPE: PRT
<213> ORGANISM: Triticum durum

<400> SEQUENCE: 1

```
Met Thr Gly Asn Arg Gly Gly Arg Arg Arg Lys Ala Gly Arg Arg Ala
1               5                   10                  15

Arg Asp Asn Asp Leu Asp Ile Ser Gln Ser Asn Ser Asp Gly Gln Asp
            20                  25                  30

Gly Ala Glu Gly Ser Gln Gln Pro Lys Arg Arg Leu Gln Arg Leu Asn
        35                  40                  45

Pro Gln Gln Thr Gln Val Leu Glu Gly Phe Phe Gly Ile Cys Ala His
    50                  55                  60

Pro Asp Glu Asn Gln Arg Met Gly Met Ser Glu Ser Thr Gly Leu Thr
65                  70                  75                  80

Met Gln Gln Val Lys Phe Trp Phe Gln Asn Lys Arg Thr His Met Lys
                85                  90                  95

His Val Thr Gly Lys Glu Glu Thr Tyr Arg Met Lys Ala Gln Asn Glu
            100                 105                 110

Met Leu Arg Glu Glu Asn Lys Arg Leu Ala Ser Ala Ala Lys Thr Ala
        115                 120                 125

Phe Cys Pro Ala Cys Val Ala Leu Pro Gly Leu Asn Pro Ser Val Glu
    130                 135                 140

Val Gln Arg Leu Arg Gln Glu Asn Glu Ser Leu Lys Gln Gln Leu Ser
145                 150                 155                 160

Gln Leu Arg Ala Glu Ala His Pro Ser Ser Ser Arg Pro Phe Gln Leu
                165                 170                 175

Asp Pro Ser Thr Glu Asn Ile Ile Gly Arg Glu Asn Asp Met Asp Ala
            180                 185                 190

Ile Ala Glu Leu Ala Gln Ser Ala Met His Glu Phe Val Val Leu Ser
        195                 200                 205
```

```
Glu Ser Gly Gly Pro Leu Trp Met Pro Val Pro Gly Gly Ser Leu Asp
    210                 215                 220

Val Leu Asn Lys Met Ala Tyr Ala Gln Thr Phe Gly Ala Gly Ser Ser
225                 230                 235                 240

Ala Asn Ala Ile Gly Phe Met Thr Glu Ala Thr Arg Ala Asp Gly Met
                245                 250                 255

Val Met Met Asp Ala Lys Gln Ile Val Asp Tyr Ile Met Asp Ser Glu
                260                 265                 270

Cys Tyr Thr Ser Phe Cys Pro Gly Leu Val Thr Ser Ala Asn Thr Thr
            275                 280                 285

Lys Val Tyr Lys Trp Pro Thr Ser Ala Gly Tyr Asn Gly Ala Met His
290                 295                 300

Leu Met Thr Val Glu Thr Val Phe Pro Ser Pro Leu Val Pro Ser Arg
305                 310                 315                 320

Lys Cys Thr Phe Val Arg Cys Cys Arg Asp Met Gln Asn Gly Thr Val
                325                 330                 335

Ile Ile Val Asp Val Ser Leu Asp Asn Gly Asp Gly Thr Phe Lys Cys
                340                 345                 350

His Lys Met Pro Ser Gly Ile Leu Ile Arg Ser Leu Asn Ser Asp Ala
            355                 360                 365

Ser Gln Val Thr Val Val Glu His Val Gln Val Asn Asp Thr Gly Val
    370                 375                 380

His Glu Leu Tyr Arg Pro Ser Leu Ser Gly Leu Met Phe Gly Ala Arg
385                 390                 395                 400

Arg Trp Val Ser Ser Ile Val Arg Gln Ser Ala Arg Met Arg Asp Leu
                405                 410                 415

Phe Ile Val Ser Lys Ser Ala Ser Asn Gly Asn Thr Asn Gly Arg Lys
                420                 425                 430

Thr Leu Met Lys Ile Ala Asp Gly Leu Leu Ala Asp Tyr Ala Ser Gly
            435                 440                 445

Ile Ala Ala Val Pro Gly Ser Gly Trp Thr Ile Leu Arg Gly Ala Gly
    450                 455                 460

Thr Glu Asp Asp Ile Arg Ile Thr Tyr Arg Lys Asn Asn Asp Asp Ser
465                 470                 475                 480

Asn Asn Ala Val Val Ser Val Cys Ala Ser Phe His Leu Pro Val Pro
                485                 490                 495

Leu Lys Val Thr Phe Asp Leu Leu Lys Asn Asn Leu Leu Arg Pro Lys
                500                 505                 510

Trp Asp Val Leu Val Asn Gly Asn Ser Val Arg Glu Val Ala Val
            515                 520                 525

Cys Lys Gly Val Gly Ala Gly Ile Asp Val Val Ser Ile Leu His
530                 535                 540

Leu Lys Asn Arg Asp Asn Ile Met Ile Leu Gln Asn Ser Gly Tyr Asp
545                 550                 555                 560

Val Ser Gly Ala Phe Met Val Tyr Cys Pro Val Asn Ile Gln Val Met
                565                 570                 575

Asn Glu Ile Met Ser Pro Ser Asn Thr Ala Glu Ser Asn Asn Val Ser
                580                 585                 590

Leu Tyr Pro Thr Gly Phe His Leu Leu Pro Val Glu Asp Thr Ala Leu
            595                 600                 605

Gly Leu Gly Glu Gly Gly Ala Thr Leu Val Thr Ala Gly Phe Gln Ile
610                 615                 620
```

```
Met Leu Lys Leu Ala Arg Gly Thr Gly Leu Tyr Pro Arg Ser Ala Ser
625                 630                 635                 640

Thr Ala Ala Gly Leu Met Thr Glu Asn Ile Ala Thr Ile Lys Lys Thr
                645                 650                 655

Leu Thr Ser Ser His Pro Ile Phe Tyr Arg Arg Gln Pro Pro Asn Asn
            660                 665                 670

Leu Ile

<210> SEQ ID NO 2
<211> LENGTH: 2645
<212> TYPE: DNA
<213> ORGANISM: Triticum durum

<400> SEQUENCE: 2
cacatcggtg ctctacattc gagtgaagta gacactagag aaatttatag ggcgtggata      60
gattctgatt tggtcgacag atcaacttgg cgagggcgtt cgatcttttg agcccaagat     120
gactggcaat cgtggtgggc gtaggagaaa ggcgggccgt cgagcacgcg acaatgactt     180
ggacatatca caaagcaact cggatggaca agatggcgcc gagggatcac aacagcccaa     240
gaggcgcctg cagaggctca ccccccagca acccaagtg cttgaagggt ttttcggcat      300
atgtgcgcac cctgacgaga atcaaaggat ggggatgagc gagtcaacag gtctcacgat     360
gcagcaagtc aagttttggt ttcagaacaa gaggacacat atgaagcatg tgactggaaa     420
agaagagacc tataggatga agcgcagaa tgagatgctg agggaggaaa acaagaggct      480
tgcatcggca gctaagactg cattctgccc cgcctgcgtt gctttaccag gactgaatcc     540
ctctgtggag gtgcagaggc taaggcagga aaatgaatca ctgaagcaac agctttcaca     600
gctgcgtgct gaagcgcatc caagttcaag ccgtcctttt caacttgacc catccacaga     660
gaatatcatt ggaagagaaa atgacatgga tgcgattgct gaactcgctc aaagtgcaat     720
gcacgagttt gtcgtcctgt ccgaatccgg cggacctctg tggatgcctg tccctggtgg     780
ttcccttgac gtgctgaaca agatggctta tgctcaaaca tttggcgcag gaagcagcgc     840
aaatgccata ggattcatga ccgaggctac tcgtgctgat ggtatggtca tgatggacgc     900
caaacagatt gtggactata tcatggactc tgagtgctac acatctttct gtcctggact     960
tgtgactagt gcaaatacca ccaaggttta caagtggcct actagtgcag gctacaatgg    1020
ggctatgcat ttgatgaccg tcgagacggt gttcccatcg ccactggtac catccaggaa    1080
atgcacattc gtgaggtgct gcagggatat gcaaaatggg acagtgatca ttgtagatgt    1140
gtctttggac aacggtgacg gcaccttcaa atgccacaaa atgccatcag gaatcctaat    1200
tcggagcctg aattccgacg ccagccaggt cactgtcgta gagcatgtcc aagtgaatga    1260
tactggtgtt cacgagctct accgcccaag cttgagcgga ctgatgttcg gagctaggcg    1320
ctgggtgtcg agcattgtgc gacagagcgc acgcatgaga gacctcttca ttgtcagcaa    1380
aagcgcctcg aacggcaaca caaatgggag gaagaccctc atgaagatag cggacggcct    1440
gctcgcagac tacgccagcg gcatcgccgc ggtccctggg agcggatgga ccattctgcg    1500
tggcgccggc acggaagacg acatcaggat cacatacagg aagaacaacg acgcagcaa    1560 caacgccgtc gtgtccgtgt gtgcgtcgtt ccatctgccg gtgccgctca aggtgacgtt    1620
tgatctgctc aagaacaacc tgttacgccc aaagtgggat gtgctggtga acggtaattc    1680
ggtgagggag gaagtcgctg tttgcaaagg cgtaggagca ggaattgatg atgttgtctc    1740
catactgcat ctcaagaaca gggacaacat catgatcctc cagaacagcg gctacgacgt    1800
```

```
gtcgggcgcg ttcatggtct actgcccagt caacatccaa gtgatgaacg agatcatgag    1860
ccctagcaac acggcggaga gcaacaatgt gtccctctac cccaccggct tccacctcct    1920
ccccgtcgag gacactgccc ttggcctcgg cgagggtgga gcaactcttg tgaccgcggg    1980
gttccagatt atgctcaagc tcgctcgtgg caccggcctg tatcctaggt ccgcgtccac    2040
ggccgccggt ctgatgacag aaaacattgc taccatcaag aagactctga ccagcagcca    2100
ccccatcttc ataggaggc agccccccaa caatctcatc tagaatgtac ccaggtaatt    2160
ctgctaattc ctgttaaact ccactaggcc tcacctagct agttcccagt aatttgctga    2220
tgacgcctgt tatttgcaca ggggcagaaa ggggagaagc gatgctggtg gaagtctgtc    2280
aaactgcatt ccgatctcct ggcgttactg caatataccc cctccgtttc ataataagtg    2340
tcgtggtttt agttcaaatt tgaactaaaa ccacgacact tactatggaa ccgagggagt    2400
atattgttat atttacttta ctacttgcga cttgctattt acaataagaa cctgcaataa    2460
tggtttaaga actagacttg tctttatcga gaaaagatcc tggcctatat atggtcgggt    2520 tttcttact ctctgcaact ttcagcttat agtaaaaact tgtgttgtaa taatggttca    2580
agaactagac ctgttgttgt cgtcgtcgtt gttgttgttg ttataaaaac ttgttttaat    2640
aatat                                                                2645

<210> SEQ ID NO 3
<211> LENGTH: 3029
<212> TYPE: DNA
<213> ORGANISM: Triticum durum

<400> SEQUENCE: 3
caccgtcttc accttcaccg tctccggtcc cttctacttc atcagcggca acaaggacaa      60
ctgcaaccgc ggcgagaagc tggtcgtcgt cgtcatgggc ccccgcgccg ccaccaacgg     120
cacctccacg cacgcggggg cgctggctcc atcgccggct gccgacaatg gcggccagtt     180
ctcgccgccg tccccgcccc ctcccttcgg catcaacatc tcgcccacgg ggaaccccga     240
ccagcagaac gccgcggccg gcaaggcggc aggtgttgcc ggcacggccg cgctcatcat     300
cgggaccatg ctctactcgc ttgtttgaat aatcacggct ttgttttac tgtccaaatt     360 atgtaccatt ggtttgattt aagcttgctc ttaatactat gttgtatcaa catttcatgt     420
aaacagtgtg gctgaactat tgcaattgat ccataatatg taaatgctgg tactgttttt     480
tttttaccat tgacaaagtg atgaaataca aagatgatta cgtgtattga aaataataac     540
gatcattgtg atagaacaag tgtatacaat accgcaaatc ttcaaattgt gcaactaacc     600
ctagaaaaca ccgcggcttg tcggtccaca tttaagcatg tcaatatata tgacacatgc     660
cggctgtgtt tgtacaagta ttttttttt cacgataaat ttgtataagt aaatatatag     720
tatgatccaa tataaaatta tcaagcacgc ttggttttac agcatagccc aaataggtgg     780
cacttttccg ctcaaagcaa cacgctaaat aaaagccatt gtaggaaata tttgtgacat     840
gctatatttg acattgcatg catgattgat gtgaatattg cgtcttcctt aaattgtagc     900
ccaattagta cgacactttg catagtactc ttagcgacta gcccaaatgc aagaaatttt     960
tcatatgcac ctttgttagc tccccggccc ttcctactct ccctgctccc ccgggctcc    1020 cgggcccctc ctctgcaccc cgcattagct tcttctgaat cctccatcgc cggccccaca    1080
ctggcctcca tctaactcac ccctcggcct ccgctccccc ttcccgcccc tccagtggc    1140 ccatattagc cccgtctgaa accccatccc aagccccac actgacctcc ctccgaacca    1200
cccctcggcc tccgctcccc cttcccgacc ccaccccctg cggcccacat tagccccgtt    1260
```

```
cgaatgcccc ataccaagcc ccacactgac ctccctctga atcacccctt ggcctccggt    1320 ccccttccc gccccgcccc ctgcggccca cattagcccc atctgaatgc accatcccaa    1380
gccccacact gacctccctc cgagtcaccc ctcggcctct gctccccctt cccgcccat    1440 ccctgcggc ccacattagc cccgtctgaa tgccccatcc taagcccac aatgacctcc    1500 ctgcgaatct cacctcggcc tccgctcccc cttcctgccc accccctgcg gcccacatta    1560
gccctgttcg aatcccctag tccaagcccc acactggcct cacccttgg cctccccac    1620 cccccccct tccggtccc tctgtggccc acattagccc cgtccaaatc ctccatcccc    1680
accactctcg cgcgtcggca cgcccacact gggccaaccc caacaactt ctaatatcac    1740 tgtgctatgg tgcccgagcg caattttat catatcatag ccatgctaat ttgacttaaa    1800
attataacaa gtaggacta tggtatcatc aataaatcta gatttatcga tgcaagttta    1860
ttcgcgtacc atagcaggcc acaatcaaaa cttctattat caacaggtta tacgtacata    1920
aatatgtggt gtcattatca atataacgtg cgtgtcacct ttttttcttt tcttgatcaa    1980
tttggctatt ttgattgaac atataatctc cttctataac ctcgcatgtc atgtgcaaac    2040
aattttccca cccaggcgtg agtgtaaaca tggaccagag gtttaggata gtgaaaagtg    2100
atttatgtaa accatcttct attgcaaata tggatgttat catatgggtg aagtggggct    2160
agctaatcat tccctaattg ttatattcaa taagtgtgtc tacattagtt tactttttatt    2220 gactacaaag tctgtttttg ttaaccattt cagcattcac aatttatgc gttgaaggtc    2280 aaatggatgt tcatgaaata atataatgta cctctaatgt gtaatatatc ctcagaactc    2340
ctaaaatcta ctacacatgt cctggtttac ctgctttact agtccttttg tttgggtcat    2400
attttaacca tgactttaac taataaatat aagttatacg tacaaaaaat atatcatgga    2460
aaactacatt caaatatgaa tccaacacta aattttttg taacatgcat taacattttg    2520
ctagtcaaat acgcggtcaa attttgaccc aaaatatgat gggactaata aacccagagg    2580
tagtaaccac ccaggctatt tcgtcctttt tttgcttacc ctgcccactc ccccaccctg    2640
tattttaatg aggtaggggt atatttggaa acaaataatt attttcctcg tattatatct    2700
catgcaaggc tgtgcaatta taagcacact aatttattgt acaaaaatta aaccaaaaga    2760
tttccatata ttcgctttat ttaggagcat tgtattagct actcttttt acaggcgtta    2820 atagctactg gagcaaaaaa aaagtgcgc aggccagggg taaggcccat atggatggct    2880
atatataggt ggcaaagaaa agggaaaca acacatcggt gctctacatt cgagtgaagt    2940
agacactaga gaaattttata gggcgtggat agattctgat ttggtcgaca gatcaacttg    3000
gcgagggcgt tcgatctttt gagcccaag                                     3029
```

<210> SEQ ID NO 4
<211> LENGTH: 4888
<212> TYPE: DNA
<213> ORGANISM: Triticum durum

<400> SEQUENCE: 4

```
atgactggca atcgtggtgg gcgtaggaga aaggcggtat aattgtttcc ctcatctcta     60
atactagctg gaagttttct tgcatgcttt cttgctactc caaagagttg tagcatgtct    120
tgttcttaga aaaattatct aacgaaatat gagtacataa gggcttgaat ttcttaggag    180
atgttgaaat atatcttgca aatcctccat ctagttcgc agaagtgcta cctgggattt    240
tttgttaatg tactttacat caactcagac atgttttca tagatctaca taatatgaat    300
```

```
gaagtttttt ctggctagag gtgcaacgac ccgctcgttg cagcaaatac catcatctgt      360
tttgacatgc attcgtattc taatccaggt tcttcatgtt catgtacttt ttttttctga      420
gaatcgttca tgtaaccaat tcactaatta tataaattcc ttgatcaagt catcgaggtt      480
atcatagccc atttgttgtt ctaatagttc ataatcaaaa gcttttccat gggagacttt      540
acagatctag tagtgtacat gcacggaatg gaaaaggcgg tacataaaaa ttacatccaa      600
acataacggc gtatcttgtc tgcacccttt gcaattgttt gcccatatat tgtactccct      660
ctgtctcaaa atataagaac gttttaaca ctacactaat gtcaaaaagg ttcttatatt       720
atgggacgga gggggtactg aagaaataac aaatcaataa tattcggctt tgcttgtgtt      780
ttccttgctt cgttcaccgc tctccctacg agccaaagtc tacttcattc ttggttttt       840 gcctttatgg aagcatgaaa agggtgtggg tagatactag agtccagatg cactatgcat      900
gcgttgcgga tgttttcaaa cataaagacg tgtttgtata cacgtatatg cccggagctt      960
gggcccactt gctctgttaa gactagcggt actgtagagc atatttcatg gtgctgtgcc     1020
acctaaaaat tccgaggcaa ttcaaagcat ggtgggcccc gcataggaca aaatccccaa     1080
gaaatactaa ttggcatctt ccaaatttac ttttcaagct atttaatatt tacagcggag     1140 cgtaatttt tgccattttg aatgcggcat gccacagcca caacgggcc gtcgagcacg       1200 cgacaatgac ttggacatat cacaaagcaa ctcggatgga caagatggcg ccgagggatc     1260
acaacagccc aagaggcgcc tgcagaggct caaccccag caaacccaag tgcttgaagg      1320
gtatgattcc caccaaagaa tttagtctaa tgaatttaac gcatccctct ttttttcat     1380 tttcctcgct tgaatgaaca ggttttcgg catatgtgcg caccctgacg agaatcaaag      1440
gatggggatg agcgagtcaa caggtctcac gatgcagcaa gtcaagtttt ggtttcagaa     1500
caagaggaca catatgaagg tctgtcctaa aacacttttc aacttgtaaa tctcagtgac     1560
acagttggtc aatatatgca tctctcaact actattacta ctgtacattg tcatatcttc     1620
acttctttag ttacagactt actgtatgta gcacagtagg atctgacatg caaaagcctt     1680
acggcggcaa tcgttctaac taattgttcc atgacacaaa ttgcagcatg tgactggaaa     1740
agaagagacc tataggatga aagcgcagaa tgagatgctg agggaggaaa acaagaggct     1800
tgcatcggca gctaagactg cattctgccc cgcctgcgtt gctttaccag gactgaatcc     1860
ctctgtggag gtgcagaggc taaggcagga aaatgaatca ctgaagcaac aggtaaataa     1920
aaccgactat aaacaagccc ttctagcatt ttcaatcagc tcaactctct ctacactttg     1980
aaacatttgg cagactgtgt tccaggcttt agtatcttaa gagcaatgct agacgtgcct     2040
atctttgaag taactttggt ggaattattc ctgtagcact aagttgccaa gtcttacaaa     2100
gattgcatct cgagttaatt ttccgtcctc ttttgagatg attgcacctc gatttacact     2160
gatgttgtat tcttcgttcg gcagctttca cagctgcgtg ctgaagcgca tccaagttca     2220
agccgtcctt ttcaacttga cccatccaca gagaatatca ttggaagaga aaatgacatg     2280
gatgcgattg ctgaactcgc tcaaagtgca atgcacgagt ttgtcgtcct gtccgaatcc     2340
ggcggaccTC tgtggatgcc tgtccctggt ggttcccttg acgtgctgaa caagatggct     2400
tatgctcaaa catttggcgc aggaagcagc gcaaatgcca taggattcat gaccgaggct     2460
actcgtgctg atggtatggt catgatggac gccaaacaga ttgtggacta tatcatggac     2520
tctgtaagtt gcctatttaa taaatcttgt cattgatgat atttcaagtc acacacacaa     2580
tttgatccca ttgttgaatg actgcaggag tgctacacat ctttctgtcc tggacttgtg     2640
actagtgcaa ataccaccaa ggtttacaag tggcctacta gtgcaggcta caatggggct     2700
```

```
atgcatttgg tatgtatgct tttctttctc tatgttttta gccaagagat gtttggcatg    2760
agtatccaat aaaaaaatac aaaattatat tactgacaaa aacaagcata tcctgaggag    2820
aaatcagtct gcctcgttac tcacagtttg tttgccttct ttctgcttgc ttgaaaacaa    2880
tagatgaccg tcgagacggt gttcccatcg ccactggtac catccaggaa atgcacattc    2940
gtgaggtgct gcagggatat gcaaaatggg acagtgatca ttgtagatgt gtctttggac    3000
aacggtgacg gcaccttcaa atgccacaaa atgccatcag gaatcctaat tcggagcctg    3060
aattccgacg ccagccaggt atggtaaaaa agactttagt aaatgaattt ctaccagtat    3120
gatgtcggca ccttactcag tgtttgattc gctccgaaac cttcttggca ggtcactgtc    3180
gtagagcatg tccaagtgaa tgatactggt gttcacgagc tctaccgccc aagcttgagc    3240
ggactgatgt tcgagctagc gcgctgggtg tcgagcattg tgcgacagag cgcacgcatg    3300
agagacctct tcattgtcag caaaagcgcc tcgaacggta attagctaga acctgcaaat    3360
attcagtcct gaaactctgt aactgaacat atcctgagaa acaaacgagt tttctattgg    3420
tttgtttcag gcaacacaaa tgggaggaag accctcatga agatagcgga cggcctgctc    3480
gcagactacg ccagcggcat cgccgcggtc cctgggagcg gatggaccat tctgcgtggc    3540
gccggcacgg aagacgacat caggatcaca tacaggaaga acaacgacga cagcaacaac    3600
gccgtcgtgt ccgtgtgtgc gtcgttccat ctgccggtgc cgctcaaggt gacgtttgat    3660
ctgctcaaga acaacctgtt acgcccaaag gtatgcaccc atgttatgtt tggcatgtgc    3720
agttctcctc tctcagcggc tagtcatgta tgtactaatg ctatgtttta ctcacacagt    3780
gggatgtgct ggtgaacggt aattcggtga gggaggaagt cgctgtttgc aaaggcgtag    3840
gagcaggaat tgatgatgtt gtctccatac tgcatctcaa ggtaccaaac acatccaatt    3900
tcagctcctc caagaatcac cacttctcct ccagtaatct tgcatctcac tcgactaact    3960
cgagtataca tacgcatgaa ggatccgccc accaggagag acagggacaa catcatgatc    4020
ctccagaaca gcggctacga cgtgtcgggc gcgttcatgg tctactgccc agtcaacatc    4080
caagtgatga acgagatcat gagccctagc aacacggcgg agagcaacaa tgtgtccctc    4140
taccccaccg gcttccacct cctccccgtc gaggacactg cccttggcct cggcgagggt    4200
ggagcaactc ttgtgaccgc ggggttccag attatgctca agctcgctcg tggcaccggc    4260
ctgtatccta ggtccgcgtc cacggccgcc ggtctgatga cagaaaacat tgctaccatc    4320
aagaagactc tgaccagcag ccaccccatc ttctatagga ggcagccccc caacaatctc    4380
atctagaatg tacccaggta attctgctaa ttcctgttaa actccactag gcctcaccta    4440
gctagttccc agtaatttgc tgatgacgcc tgttatttgc acaggggcag aaaggggaga    4500
agcgatgctg gtggaagtct gtcaaactgc attccgatct cctggcgtta ctgcaatata    4560
ccccctccgt ttcataataa gtgtcgtggt tttagttcaa atttgaacta aaaccacgac    4620
acttactatg gaaccgaggg agtatattgt tatatttact ttactacttg cgacttgcta    4680
tttacaataa gaacctgcaa taatggttta agaactagac ttgtctttat cgagaaaaga    4740
tcctggccta tatatggtcg ggttttcttt actctctgca actttcagct tatagtaaaa    4800
acttgtgttg taataatggt tcaagaacta gacctgttgt tgtcgtcgtc gttgttgttg    4860
ttgttataaa aacttgttttt aataatat                                      4888
```

<210> SEQ ID NO 5
<211> LENGTH: 9000
<212> TYPE: DNA

<213> ORGANISM: Triticum durum

<400> SEQUENCE: 5

```
aggcaagtta cacccactat taccatccct aatctaatct catcgactaa tgcgtgcata      60
tccgtggacg ggggctccgc ccctcgcccg gataccgcgc attacccata gcaccgatcg     120
acagcacact gcactaatgc atgtgtatcc gtccgcgagg agccaaattg tggatatatg     180
gagttgcatc gcccgcatcc acacgcgata tatgcgtata tttggtgagc ttgccgcgat     240
atatgtgcac aaatgctctg cattaatcga tatatttcgg cgtcggatgc aactccccgg     300
caagatatat ctgcattaat cattaatctg cacaaacgcg tttgctttcg gcgccgcccg     360
cgttacttct agttttttgta ccttttcttt tgttcaagct gtaacggcta tcgctatggc     420
ttcaagatag atgtgacgac ggtctcccta tctcgaacgc actggcaagg tagaccggtg     480
aaggcgcctc cccggccgca gcctcgtttg tccgcatcag gcatgccggc aaatgaccaa     540
actagacacc cgaccttgtc aatattacca ccgctgccac ttgattagca ctaactaatg     600
aagccgtaac aacatggcat taattaatta ctctccattt tcactgtgca gtagtaaagc     660
taatcgaatt tttaccgcgt ctgtgcatgc atgcagcgtt cacgtaccag cccggcagcg     720
actcggtgct catcgtcgac aagaaggcgt acgacgcctg cgacaccggt tcgccggtgg     780
acaccttctc cgacggcaac accgtcttca ccttcaccgt ctccggtccc ttctacttca     840
tcagcggcaa caaggacaac tgcaaccgcg gcgagaagct ggtcgtcgtc gtcatgggcc     900
ccgcgccgc caccaacggc acctccacgc acgcgggggc gctggctcca tcgccggctg     960
ccgacaatgg cggccagttc tcgccgccgt ccccgccccc tcccttcggc atcaacatct    1020
cgcccacggg gaaccccgac cagcagaacg ccgcggccgg caaggcggca ggtgttgccg    1080
gcacggccgc gctcatcatc gggaccatgc tctactcgct tgtttgaata atcacggctt    1140
tgttttact gtccaaatta tgtaccattg gtttgattta agcttgctct taatactatg    1200
ttgtatcaac atttcatgta aacagtgtgg ctgaactatt gcaattgatc cataatatgt    1260
aaatgctggt actgttttttt ttttaccatt gacaaagtga tgaaatacaa agatgattac    1320
gtgtattgaa ataataacg atcattgtga tagaacaagt gtatacaata ccgcaaatct    1380
tcaaattgtg caactaaccc tagaaaacac cgcggcttgt cggtccacat ttaagcatgt    1440
caatatatat gacacatgcc ggctgtgttt gtacaagtat ttttttttttc acgataaatt    1500
tgtataagta aatatatagt atgatccaat ataaaattat caagcacgct tggttttaca    1560
gcatagccca ataggtggc acttttccgc tcaaagcaac acgctaaata aaagccattg    1620
taggaaatat ttgtgacatg ctatatttga cattgcatgc atgattgatg tgaatattgc    1680
gtcttcctta aattgtagcc caattagtac gacacttttgc atagtactct tagcgactag    1740
cccaaatgca agaaatttttt catatgcacc tttgttagct ccccggccct tcctactctc    1800
cctcgctccc ccgggctccc gggcccctcc tctgcacccc gcattagctt cttctgaatc    1860
ctccatcgcc ggccccacac tggcctccat ctaactcacc cctcggcctc cgctccccct    1920
tcccgcccct cccagtggcc catattagcc ccgtctgaaa ccccatcccc aagcccaca    1980
ctgacctccc tccgaaccac ccctcggcct ccgctccccc ttcccgaccc cacccctgc    2040
ggcccacatt agcccgttc gaatgcccca taccaagccc cacactgacc tccctctgaa    2100
tcaccccttg gctccggtc cccttcccg ccccgcccc tgcggccac attagcccca    2160
tctgaatgca ccatcccaag ccccacactg acctccctcc gagtcacccc tcggcctctg    2220
ctcccccttc ccgcccatc ccctgcggcc cacattagcc ccgtctgaat gccccatcct    2280
```

```
aagccccaca atgacctccc tgcgaatctc acctcggcct ccgctccccc ttcctgccca   2340
ccccctgcgg cccacattag ccctgttcga atccctagt ccaagcccca cactggcctc    2400
accccttggc ctcccccacc cccccccctt cccggtccct ctgtggccca cattagcccc   2460
gtccaaatcc tccatcccca ccactctcgc gcgtcggcac gcccacactg gccaaccccc   2520
aacaactttc taatatcact gtgctatggt gcccgagcgc aattttttatc atatcatagc  2580 catgctaatt tgacttaaaa ttataacaaa gtaggactat ggtatcatca ataaatctag   2640
atttatcgat gcaagtttat tcgcgtacca tagcaggcca caatcaaaac ttctattatc   2700
aacaggttat acgtacataa atatgtggtg tcattatcaa tataacgtgc gtgtcacctt   2760
tttttctttt cttgatcaat ttggctattt tgattgaaca tataatctcc ttctataacc   2820
tcgcatgtca tgtgcaaaca attttcccac ccaggcgtga gtgtaaacat ggaccagagg   2880
tttaggatag tgaaaagtga tttatgtaaa ccatcttcta ttgcaaatat ggatgttatc   2940
atatgggtga agtggggcta gctaatcatt ccctaattgt tatattcaat aagtgtgtct   3000
acattagttt acttttattg actacaaagt ctgttttttgt taaccatttc agcattcaca  3060 atttttatgcg ttgaaggtca aatggatgtt catgaaataa tataatgtac ctctaatgtg  3120
taatatatcc tcagaactcc taaaatctac tacacatgtc ctggtttacc tgctttacta   3180
gtccttttgt ttgggtcata ttttaaccat gactttaact aataaatata agttatacgt   3240
acaaaaaata tatcatggaa aactacattc aaatatgaat ccaacactat aatttttgt    3300 aacatgcatt aacattttgc tagtcaaata cgcggtcaaa ttttgaccca aaatatgatg   3360
ggactaataa acccagaggt agtaaccacc caggctattt tcgtccttttt ttgcttaccc  3420 tgcccactcc cccaccctgt attttaatga ggtaggggta tatttggaaa caaataatta   3480
ttttcctcgt attatatctc atgcaaggct gtgcaattat aagcacacta atttattgta   3540
caaaaattaa accaaaagat ttccatatat tcgctttatt taggagcatt gtattagcta   3600 ctcttttttta caggcgttaa tagctactgg agcaaaaaaa aaagtgcgca ggccaggggt  3660
aaggcccata tggatggcta tatataggtg gcaaagaaaa ggggaaacaa cacatcggtg   3720
ctctacattc gagtgaagta gacactagag aaatttatag ggcgtggata gattctgatt   3780
tggtcgacag atcaacttgg cgagggcgtt cgatcttttg agcccaagat gactggcaat   3840
cgtggtgggc gtaggagaaa ggcggtataa ttgtttccct catctctaat actagctgga   3900
agttttcttg catgctttct tgctactcca aagagttgta gcatgtcttg ttcttagaaa   3960
aattatctaa cgaaatatga gtacataagg gcttgaattt cttaggagat gttgaaatat   4020
atcttgcaaa tcctccatct agtttcgcag aagtgctacc tgggattttt tgttaatgta   4080
ctttacatca actcagacat gttttttcata gatctacata atatgaatga agttttttct  4140
ggctagaggt gcaacgaccc gctcgttgca gcaaatacca tcatctgttt tgacatgcat   4200
tcgtattcta atccaggttc ttcatgttca tgtacttttt ttttctgaga atcgttcatg   4260
taaccaattc actaattata taaattcctt gatcaagtca tcgaggttat catagcccat   4320
ttgttgttct aatagttcat aatcaaaagc ttttccatgg gagactttac agatctagta   4380
gtgtacatgc acggaatgga aaaggcggta cataaaaatt acatccaaac ataacggcgt   4440
atcttgtctg cacccttttgc aattgtttgc ccatatattg tactccctct gtctcaaaat  4500
ataagaacgt ttttaacact acactaatgt caaaaaggtt cttatattat gggacggagg   4560
gggtactgaa gaaataacaa atcaataata ttcggctttg cttgtgtttt ccttgcttcg   4620
```

-continued

```
ttcaccgctc tccctacgag ccaaagtcta cttcattctt ggttttttgc ctttatggaa    4680
gcatgaaaag ggtgtgggta gatactagag tccagatgca ctatgcatgc gttgcggatg    4740
ttttcaaaca taaagacgtg tttgtataca cgtatatgcc cggagcttgg gcccacttgc    4800
tctgttaaga ctagcggtac tgtagagcat atttcatggt gctgtgccac ctaaaaattc    4860
cgaggcaatt caaagcatgg tgggccccgc ataggacaaa atccccaaga aatactaatt    4920
ggcatcttcc aaatttactt ttcaagctat ttaatattta cagcggagcg taattttttg    4980
ccattttgaa tgcggcatgc cacagccaca acagggccgt cgagcacgcg acaatgactt    5040
ggacatatca caaagcaact cggatggaca agatggcgcc gagggatcac aacagcccaa    5100
gaggcgcctg cagaggctca accccagca aacccaagtg cttgaagggt atgattccca    5160
ccaaagaatt tagtctaatg aatttaacgc atccctcttt ttttcattt cctcgcttg    5220 aatgaacagg ttttcggca tatgtgcgca ccctgacgag aatcaaagga tggggatgag    5280
cgagtcaaca ggtctcacga tgcagcaagt caagttttgg tttcagaaca agaggacaca    5340
tatgaaggtc tgtcctaaaa cacttttcaa cttgtaaatc tcagtgacac agttggtcaa    5400
tatatgcatc tctcaactac tattactact gtacattgtc atatcttcac ttctttagtt    5460
acagacttac tgtatgtagc acagtaggat ctgacatgca aaagcttac ggcggcaatc    5520 gttctaacta attgttccat gacacaaatt gcagcatgtg actggaaaag aagagaccta    5580
taggatgaaa gcgcagaatg agatgctgag ggaggaaaac aagaggcttg catcggcagc    5640
taagactgca ttctgccccg cctgcgttgc tttaccagga ctgaatccct ctgtggaggt    5700
gcagaggcta aggcaggaaa atgaatcact gaagcaacag gtaaataaaa ccgactataa    5760
acaagccctt ctagcatttt caatcagctc aactctctct acactttgaa acatttggca    5820
gactgtgttc caggctttag tatcttaaga gcaatgctag acgtgcctat ctttgaagta    5880
actttggtgg aattattcct gtagcactaa gttgccaagt cttacaaaga ttgcatctcg    5940
agttaatttt ccgtcctctt ttgagatgat tgcacctcga tttacactga tgttgtattc    6000
ttcgttcggc agctttcaca gctgcgtgct gaagcgcatc caagttcaag ccgtcctttt    6060
caacttgacc catccacaga gaatatcatt ggaagagaaa atgacatgga tgcgattgct    6120
gaactcgctc aaagtgcaat gcacgagttt gtcgtcctgt ccgaatccgg cggacctctg    6180
tggatgcctg tccctggtgg ttcccttgac gtgctgaaca agatggctta tgctcaaaca    6240
tttggcgcag gaagcagcgc aaatgccata ggattcatga ccgaggctac tcgtgctgat    6300
ggtatggtca tgatggacgc caaacagatt gtggactata tcatggactc tgtaagttgc    6360
ctatttaata aatcttgtca ttgatgatat ttcaagtcac acacacaatt tgatcccatt    6420
gttgaatgac tgcaggagtg ctacacatct ttctgtcctg gacttgtgac tagtgcaaat    6480
accaccaagg tttacaagtg gcctactagt gcaggctaca atggggctat gcatttggta    6540
tgtatgcttt tctttctcta tgttttagc caagagatgt ttggcatgag tatccaataa    6600
aaaaatacaa aattatatta ctgacaaaaa caagcatatc ctgaggagaa atcagtctgc    6660
ctcgttactc acagtttgtt tgccttctttt ctgcttgctt gaaaacaata gatgaccgtc    6720
gagacggtgt tccatcgcc actggtacca tccaggaaat gcacattcgt gaggtgctgc    6780
agggatatgc aaaatgggac agtgatcatt gtagatgtgt ctttggacaa cggtgacggc    6840
accttcaaat gccacaaaat gccatcagga atcctaattc ggagcctgaa ttccgacgcc    6900
agccaggtat ggtaaaaaag actttagtaa atgaatttct accagtatga tgtcggcacc    6960
ttactcagtg tttgattcgc tccgaaacct tcttggcagg tcactgtcgt agagcatgtc    7020
```

-continued

```
caagtgaatg atactggtgt tcacgagctc taccgcccaa gcttgagcgg actgatgttc    7080
ggagctaggc gctgggtgtc gagcattgtg cgacagagcg cacgcatgag agacctcttc    7140
attgtcagca aaagcgcctc gaacggtaat tagctagaac ctgcaaatat tcagtcctga    7200
aactctgtaa ctgaacatat cctgagaaac aaacgagttt tctattggtt tgtttcaggc    7260
aacacaaatg ggaggaagac cctcatgaag atagcggacg gcctgctcgc agactacgcc    7320
agcggcatcg ccgcggtccc tgggagcgga tggaccattc tgcgtggcgc cggcacggaa    7380
gacgacatca ggatcacata caggaagaac aacgacgaca gcaacaacgc cgtcgtgtcc    7440
gtgtgtgcgt cgttccatct gccggtgccg ctcaaggtga cgtttgatct gctcaagaac    7500
aacctgttac gcccaaaggt atgcacccat gttatgtttg gcatgtgcag ttctcctctc    7560
tcagcggcta gtcatgtatg tactaatgct atgtttcact cacacagtgg gatgtgctgg    7620
tgaacggtaa ttcggtgagg aggaagtcg ctgtttgcaa aggcgtagga gcaggaattg    7680
atgatgttgt ctccatactg catctcaagg taccaaacac atccaatttc agctcctcca    7740
agaatcacca cttctcctcc agtaatcttg catctcactc gactaactcg agtatacata    7800
cgcatgaagg atccgcccac cagggagaac agggacaaca tcatgatcct ccagaacagc    7860
ggctacgacg tgtcgggcgc gttcatggtc tactgcccag tcaacatcca agtgatgaac    7920
gagatcatga gccctagcaa cacggcggag agcaacaatg tgtccctcta ccccaccggc    7980
ttccacctcc tcccgtcga ggacactgcc cttggcctcg gcgagggtgg agcaactctt    8040
gtgaccgcgg ggttccagat tatgctcaag ctcgctcgtg gcaccggcct gtatcctagg    8100
tccgcgtcca cggccgccgg tctgatgaca gaaaacattg ctaccatcaa gaagactctg    8160
accagcagcc accccatctt ctataggagg cagccccca acaatctcat ctagaatgta    8220
cccaggtaat tctgctaatt cctgttaaac tccactaggc ctcacctagc tagttcccag    8280
taatttgctg atgacgcctg ttatttgcac aggggcagaa aggggagaag cgatgctggt    8340
ggaagtctgt caaactgcat tccgatctcc tggcgttact gcaatatacc ccctccgttt    8400
cataataagt gtcgtggttt tagttcaaat ttgaactaaa accacgacac ttactatgga    8460
accgagggag tatattgtta tatttacttt actacttgcg acttgctatt tacaataaga    8520
acctgcaata atggtttaag aactagactt gtctttatcg agaaaagatc ctggcctata    8580
tatggtcggg ttttctttac tctctgcaac tttcagctta tagtaaaaac ttgtgttgta    8640
ataatggttc aagaactaga cctgttgttg tcgtcgtcgt tgttgttgtt gttataaaaa    8700
cttgttttaa taatatgttc atgaaattct tattgacatg ttaaaacttc agttcagtga    8760
atgtgttgga ttttcaaaag aacatgatac agatacagca taatggttct ctttcggtta    8820
ctacagacta agtcttaggt tttcatatag caacataaaa gaaaaccctg cacaatagca    8880
cattgttact accactgcat gcatatcaga tactccctct gttcctaaat atttgtcttt    8940
ttagagattc aaatgcacta tcacatacgg atgtatatag acatatttta agtgtagatt    9000
```

<210> SEQ ID NO 6
<211> LENGTH: 670
<212> TYPE: PRT
<213> ORGANISM: Triticum aestivum

<400> SEQUENCE: 6

Met Pro Gly Asn Arg Gly Gly Arg Arg Lys Ala Gly Arg Arg Ala
1               5                   10                  15

Arg Asp Asn Glu Leu Asp Ile Pro Gln Ser Asn Ser Asp Gly His Asp

```
                    20                  25                  30
Gly Ala Glu Gly Ser Gln Pro Lys Arg Arg Leu Gln Arg Leu Asn Pro
                35                  40                  45
Gln Gln Thr Gln Val Leu Glu Gly Phe Phe Ser Ile Cys Ala His Pro
            50                  55                  60
Asp Glu Asn Gln Arg Met Gly Leu Ser Glu Ser Thr Gly Leu Ser Met
 65                  70                  75                  80
Gln Gln Val Lys Phe Trp Phe Gln Asn Lys Arg Thr Tyr Met Lys His
                85                  90                  95
Leu Thr Gly Lys Glu Glu Ser Tyr Arg Met Lys Ala Gln Asn Glu Met
                100                 105                 110
Leu Arg Glu Glu Asn Lys Arg Leu Ala Ser Ala Lys Ala Ser Phe
                115                 120                 125
Cys Pro Ser Cys Val Ala Leu Pro Gly Gln Asn Pro Ser Val Glu Val
            130                 135                 140
Gln Arg Leu Lys Glu Glu Asn Glu Ser Leu Arg Gln Gln Val Ser Gln
145                 150                 155                 160
Leu Arg Ala Glu Ala His Gln Leu Gly Pro Ile His Ser Lys Tyr His
                165                 170                 175
Trp Arg Glu Asn Asp Ile Asp Ala Ile Ala Glu Leu Val Gln Asn Ala
                180                 185                 190
Met His Glu Phe Val Val Leu Ser Glu Ser Gly Gly Pro Leu Trp Met
            195                 200                 205
Pro Val Pro Gly Gly Ser Leu Asp Leu Leu Asn Lys Val Ala Tyr Ala
            210                 215                 220
Gln Thr Phe Gly Ala Arg Ser Ser Ala Asn Ala Ile Gly Phe Arg Val
225                 230                 235                 240
Glu Ala Thr Arg Ala Asp Gly Met Val Met Glu Ala Lys Gln Ile
                245                 250                 255
Val Asp Tyr Ile Met Asp Ser Glu Cys Tyr Thr Ser Phe Cys Pro Gly
                260                 265                 270
Thr Leu Thr Ser Ala Lys Thr Thr Lys Ile Tyr Lys Trp Pro Thr Asn
            275                 280                 285
Ala Gly Tyr Asn Gly Ala Met His Leu Met Thr Ala Glu Thr Val Phe
            290                 295                 300
Pro Ser Pro Leu Val Pro Ser Arg Lys Cys Thr Phe Val Arg Cys Cys
305                 310                 315                 320
Arg Gly Met Gln Asn Gly Thr Val Ile Ile Val Asp Val Ser Leu Asp
                325                 330                 335
Asn Gly Asp Gly Thr Phe Phe Lys Cys Arg Lys Met Pro Ser Gly Leu
                340                 345                 350
Leu Ile Arg Ser Leu Asn Ser Asp Ala Ser Gln Val Thr Val Ile Glu
                355                 360                 365
His Val Gln Val Asn Asp Ala Gly Val His Glu Leu Tyr Arg Pro Thr
            370                 375                 380
Leu Ser Gly Leu Met Phe Gly Ala Arg Arg Trp Leu Ser Ser Ile Glu
385                 390                 395                 400
Arg Gln Ser Ala Arg Met Arg Asp Leu Phe Leu Leu Thr Gln Ser Thr
                405                 410                 415
Ser Ala Ala Asn Met Asn Gly Arg Lys Thr Leu Met Lys Ile Ala Asp
                420                 425                 430
Asp Leu Leu Ala Gly Tyr Ala Asn Gly Ile Ala Ala Val Pro Gly Gly
            435                 440                 445
```

```
Arg Trp Thr Ile Leu Arg Gly Ala Gly Thr Glu Asp Asp Ile Arg Val
            450                 455                 460

Thr Tyr Arg Arg Lys Arg Tyr Asp Asp Asp Thr Ala Val Val Ser Val
465                 470                 475                 480

Cys Ala Ala Phe His Leu Pro Leu Pro Leu Arg Met Ala Phe Asp Leu
                485                 490                 495

Leu Arg Asn Ile Gln Leu Arg Pro Lys Trp Asp Val Leu Val Asn Gly
                500                 505                 510

Asn Ser Val Arg Glu Glu Val Ala Val Cys Lys Gly Val Gly Gly Phe
            515                 520                 525

Asp Asp Val Ser Ile Leu His Ile Lys His Asn Ala Glu Asn Asn Glu
            530                 535                 540

Asn Ile Met Ile Leu Gln Asn Ser Gly Tyr Asp Val Ser Gly Ala Phe
545                 550                 555                 560

Met Ile Tyr Cys Pro Val Asp Ile Gln Leu Met Asn Glu Ile Met Ser
                565                 570                 575

Pro Ser Asp Met Gly Glu Ser Asn Lys Val Ser Leu Tyr Pro Thr Gly
                580                 585                 590

Phe Ser Leu Leu Pro Val Asp Asp Ser Ala Leu Gly Leu Gly Glu Gly
            595                 600                 605

Gly Ala Thr Leu Val Thr Ala Gly Tyr Gln Ile Leu Leu Lys Leu Ala
            610                 615                 620

Arg Gly Thr Gly Leu Tyr Pro Arg Ser Val Ser Thr Ala Val Ser Leu
625                 630                 635                 640

Met Thr Glu Asn Ile Ala Thr Ile Arg Lys Thr Leu Thr Asn Ser His
                645                 650                 655

Pro Ile Phe Tyr Lys Lys Arg Gln Ser Pro Asn Asn Leu Gly
                660                 665                 670
```

<210> SEQ ID NO 7
<211> LENGTH: 2569
<212> TYPE: DNA
<213> ORGANISM: Triticum aestivum

<400> SEQUENCE: 7

```
gacatcggtg ctctacatcc gagtgaagta gacactagag aaactcatag ggcgtggttc    60
gattctgatt tggttgatag atcaacttgg cgagggcatc cggccaagat gcctggcaat   120
cgtggtgggc gtaggcgaaa ggcgggccgt cgagcacgcg acaatgagtt ggacatacca   180
caaagcaact ctgatggaca tgatggcgct gagggatcac aacccaagag cgcctacag    240
aggctcaacc cccagcaaac ccaagtactt gaagggtttt tcagcatatg tgcacaccct   300
gatgaaaatc aaaggatggg gttgagcgag tcgacgggac tttcgatgca gcaagtcaag   360
ttttggtttc aaaacaagag gacatacatg aagcatctga ctggaaaaga agagagctat   420
aggatgaaag cgcagaatga gatgctgagg gaggaaaaca gaggcttgc atcggcagct   480
aaggcttcat tttgccccctc ctgcgttgct ttaccaggac agaatccctc tgtagaggtg   540
caaaggctga aggaggaaaa tgagtcgctg aggcaacagg tatcacagtt gcgtgctgaa   600
gcacatcaac ttggacccat ccacagtaaa tatcattgga gagaaaatga catagatgcg   660
attgctgaac tggttcaaaa tgcaatgcac gagtttgtcg ttttgtccga atccggtgga   720
cctctgtgga tgcctgtccc tggtggttcc cttgacttgc tgaacaaggt ggcttatgct   780
caaacctttg gtgcaagaag cagtgcaaat gccataggat tcagggtcga ggctactcgt   840
```

```
gctgatggta tggtcatgat ggaggccaaa cagattgtgg actatatcat ggattctgag      900
tgctatacat ctttctgtcc tggaactctg actagtgcaa aaaccaccaa gatttacaag      960
tggcctacta atgcaggcta caatggggcc atgcatttga tgaccgccga gacggtgttc     1020
ccatcacccc tggtgccatc taggaaatgc acattcgtga ggtgctgcag ggggatgcaa     1080
aatgggacag tgatcatcgt tgacgtgtct ttggacaacg gtgacggaac cttcttcaaa     1140
tgccgcaaaa tgccatcagg cctactaatt cggagcctga actccgacgc cagccaggtc     1200
actgtcatag agcatgttca agtaaatgat gctggtgttc acgagctcta ccgcccaacc     1260
ttgagcgggc tcatgttcgg agctaggcgc tggttgtcga gcattgaacg acagagcgca     1320
cgcatgagag acctcttcct tttaacccaa agcacctcgg ccgccaacat gaatgggagg     1380
aagaccctca tgaagatagc ggacgacctg ctcgcgggct acgccaatgg catcgccgct     1440
gtccctgggg gcagatggac cattctgcgt ggcgctggca cagaagatga catcagggtc     1500
acctacagga ggaaaagata cgacgacgac accgccgtcg tgtccgtgtg cgcggccttc     1560
catctgccct tgccgctcag gatggcgttt gatctgctca ggaacatcca gttgcgccca     1620
aagtgggatg tgctggtgaa cggtaattcc gtgagggagg aagtcgctgt ttgcaaaggc     1680
gtaggaggat ttgatgatgt ctccatactg catatcaagc acaacgcgga gaacaacgaa     1740
aacatcatga tcctccagaa cagcggctac gacgtgtcgg gcgcgttcat gatctactgc     1800
ccggtcgaca tccaactgat gaacgagatc atgagcccta gtgacatggg ggagagcaac     1860
aaggtgtctc tctaccccac tggcttctcc ctcctccccg tcgacgactc tgcccttggc     1920
ctcggcgagg tggagcaac tcttgtgacc gcggggtacc agattctgct caagctcgct     1980
cgtggcaccg gcctgtatcc taggtccgtg tccacggccg tcagtctgat gactgaaaac     2040
attgccacca tcaggaagac tctgaccaac agccaccccca tcttctataa gaaaaggcag     2100
tcccccaaca atctcggcta aaatgtaccc aggggcagaa aggggagaag cggtcgatgc     2160
tggtggaagt ctgtcaaact gcatttcgat ctccaggcgt tactgcaata tacccctcc     2220 gtttcataat aagtgttgtg gccctagttc aaagttgaac ttaaaccaca acacttactc     2280
tggaacagac ggagtatatt gttatattta ctttactact tgcgattttc tatttacaat     2340 aaaagaaacct gtaataatgg attaagtact agacatgtct ttatcaagaa aagaacccgg     2400
cctatatatg gtgcaggttt gctttactct ttgtgagttt cagcttatat taaaaacttg     2460
ttgtaataat tgttcaagaa ctagaccagt tgttgttgat gatgatgttg ttgttgttat     2520
gctatacttt tataataaaa tttgttgtaa taatgtgttc atgggaaaa              2569
```

<210> SEQ ID NO 8
<211> LENGTH: 7
<212> TYPE: DNA
<213> ORGANISM: Triticum durum

<400> SEQUENCE: 8 tgcaaag                                                                  7

<210> SEQ ID NO 9
<211> LENGTH: 8
<212> TYPE: DNA
<213> ORGANISM: Triticum durum

<400> SEQUENCE: 9 catgcatg                                                                 8

```
<210> SEQ ID NO 10
<211> LENGTH: 7
<212> TYPE: DNA
<213> ORGANISM: Triticum durum
<220> FEATURE:
<221> NAME/KEY: misc_feature
<222> LOCATION: (5)..(6)
<223> OTHER INFORMATION: n is a, c, g, or t

<400> SEQUENCE: 10 acacnng                                                                    7

<210> SEQ ID NO 11
<211> LENGTH: 6
<212> TYPE: DNA
<213> ORGANISM: Triticum durum
<220> FEATURE:
<221> NAME/KEY: misc_feature
<222> LOCATION: (3)..(4)
<223> OTHER INFORMATION: n is a, c, g, or t

<400> SEQUENCE: 11 canntg                                                                     6

<210> SEQ ID NO 12
<211> LENGTH: 8
<212> TYPE: DNA
<213> ORGANISM: Triticum durum

<400> SEQUENCE: 12 cacctcca                                                                   8

<210> SEQ ID NO 13
<211> LENGTH: 6
<212> TYPE: DNA
<213> ORGANISM: Triticum durum

<400> SEQUENCE: 13 tacgta                                                                     6

<210> SEQ ID NO 14
<211> LENGTH: 6
<212> TYPE: DNA
<213> ORGANISM: Triticum durum

<400> SEQUENCE: 14 cctttt                                                                     6

<210> SEQ ID NO 15
<211> LENGTH: 9
<212> TYPE: DNA
<213> ORGANISM: Artificial Sequence
<220> FEATURE:
<223> OTHER INFORMATION: synthetic Y1H bait sequence

<400> SEQUENCE: 15 cattaaatg                                                                  9

<210> SEQ ID NO 16
<211> LENGTH: 683
<212> TYPE: PRT
<213> ORGANISM: Triticum durum

<400> SEQUENCE: 16

Met Thr Gly Asn Arg Gly Gly Arg Arg Arg Lys Ala Pro Gln Gln Asp
1               5                   10                  15
```

-continued

Arg Pro Ala Arg Asp Asn Asp Leu Asp Ile Ser Gln Gly Asn Ser Asp
            20                  25                  30

Gly Gln Asp Gly Ala Glu Gly Ser Gln Pro Lys Arg Arg Leu Gln Arg
        35                  40                  45

Leu Thr Pro Gln Gln Thr Gln Val Leu Glu Gly Phe Phe Gly Ile Cys
 50                  55                  60

Ala His Pro Asp Glu Asn Gln Arg Met Gly Met Ser Glu Ser Thr Gly
 65                  70                  75                  80

Leu Thr Met Gln Gln Val Arg Phe Trp Phe Gln Asn Lys Arg Thr His
                85                  90                  95

Met Lys His Val Thr Gly Lys Glu Glu Thr Tyr Arg Met Lys Ala Gln
            100                 105                 110

Asn Glu Met Leu Arg Glu Glu Asn Lys Arg Leu Ala Ser Ala Ala Lys
        115                 120                 125

Thr Ser Phe Cys Pro Ser Cys Val Ala Leu Pro Gly Leu Ser Pro Ser
130                 135                 140

Gly Glu Val Gln Arg Leu Arg Gln Glu Asn Glu Gln Leu Lys Gln Gln
145                 150                 155                 160

Leu Ser Gln Leu Arg Ala Glu Ala His Pro Ser Ser Ser Arg Pro Phe
                165                 170                 175

Gln Leu Asp Pro Ser Met Glu Asn Ile Thr Gly Arg Glu Asn Asp Met
            180                 185                 190

Asp Ala Ile Ala Glu Leu Ala Gln Ser Ala Met His Glu Phe Val Val
        195                 200                 205

Leu Ala Glu Ala Gly Gly Pro Leu Trp Met Pro Val Pro Gly Gly Ser
    210                 215                 220

Phe Asp Val Leu Asn Lys Met Ala Tyr Ala Gln Thr Phe Gly Ala Arg
225                 230                 235                 240

Ser Ser Ala Asn Val Ile Leu Gly Phe Met Thr Glu Ala Thr Arg Ala
                245                 250                 255

Asp Asp Met Val Met Met Asp Ala Lys Gln Ile Val Asp Tyr Ile Met
            260                 265                 270

Asp Ser Glu Cys Tyr Thr Ser Phe Cys Pro Gly Leu Leu Thr Ser Ala
        275                 280                 285

Asn Thr Thr Lys Ile Tyr Lys Trp Pro Thr Ser Ala Gly Tyr Asn Gly
    290                 295                 300

Ala Met His Leu Val Thr Val Glu Thr Val Phe Pro Ser Pro Leu Val
305                 310                 315                 320

Pro Ser Arg Lys Cys Thr Phe Val Arg Cys Cys Arg Asp Met Gln Asn
                325                 330                 335

Gly Thr Val Ile Ile Val Asp Val Ser Leu Asp Asn Gly Asp Gly Thr
            340                 345                 350

Val Lys Cys His Lys Met Pro Ser Gly Val Leu Val Arg Ser Leu Asn
        355                 360                 365

Ser Asp Ala Ser Gln Val Thr Val Ile Glu His Val Gln Val Asn Asp
    370                 375                 380

Thr Gly Leu His Glu Leu Tyr Arg Pro Ser Leu Ser Gly Leu Met Phe
385                 390                 395                 400

Gly Ala Arg Arg Trp Val Ser Ser Ile Val Arg Gln Ser Ala Arg Met
                405                 410                 415

Arg Asp Leu Phe Val Val Ser Lys Ser Ala Ser Asn Gly Asn Thr Asn
            420                 425                 430

Gly Arg Lys Thr Leu Met Lys Ile Ala Asp Gly Leu Leu Ala Gly Tyr
            435                 440                 445

Ala Ser Gly Ile Ala Ala Val Pro Gly Gly Gly Trp Thr Ile Leu Arg
        450                 455                 460

Gly Ala Gly Thr Glu Asp Asp Ile Arg Ile Ser Tyr Arg Arg Asn Asn
465                 470                 475                 480

Asp Asp Ser Asn Thr Ala Ile Val Ser Val Cys Ala Ser Phe His Leu
                485                 490                 495

Pro Val Pro His Arg Val Thr Phe Asp Leu Leu Lys Asn Asn Leu Leu
            500                 505                 510

Arg Pro Lys Trp Asp Val Leu Val Asn Gly Asn Ser Val Arg Glu Glu
        515                 520                 525

Val Ala Val Cys Lys Gly Val Gly Gly Gly Ile Asp Asp Val Val Ser
    530                 535                 540

Ile Leu His Leu Lys Asp Pro Pro Thr Gly Glu Asn Arg Asp Asn Ile
545                 550                 555                 560

Met Ile Leu Gln Asn Ser Ser Tyr Asp Val Ser Gly Ala Phe Met Val
                565                 570                 575

Tyr Cys Pro Val Asn Ile Gln Leu Met Asn Glu Ile Met Ser Pro Ser
            580                 585                 590

Asp Thr Ala Glu Ser Asn Lys Val Ser Leu Tyr Pro Thr Gly Phe Tyr
        595                 600                 605

Leu Leu Pro Val Glu Asp Thr Ala Leu Gly Leu Glu Gly Gly Ala
    610                 615                 620

Thr Leu Val Thr Val Gly Phe Gln Ile Met Leu Lys Leu Ala Arg Gly
625                 630                 635                 640

Thr Gly Leu Tyr Pro Arg Ser Ala Ser Thr Ala Val Gly Leu Met Thr
                645                 650                 655

Glu Asn Ile Ala Thr Ile Lys Lys Thr Leu Thr Ser Ser His Pro Ile
            660                 665                 670

Phe Tyr Arg Arg Gln Pro Pro Asn Asn Leu Ile
        675                 680

<210> SEQ ID NO 17
<211> LENGTH: 2052
<212> TYPE: DNA
<213> ORGANISM: Triticum durum

<400> SEQUENCE: 17
atgactggca atcgtggtgg gcgtaggaga aaggcgccgc aacaggaccg tccagcacgc     60
gacaatgact tggacatatc acaaggcaac tccgatggac aagatggcgc cgagggtca    120 cagcccaaga ggcgcctgca gaggctcacc ccccagcaaa cccaagtgct tgaagggttt    180
ttcggcatat gcgcgcaccc tgacgagaat caaaggatgg ggatgagcga gtcgacaggt    240
ctcacgatgc agcaagtcag gttttggttt cagaacaaga ggacacatat gaagcatgtg    300
actggaaaag aagagaccta caggatgaaa gcgcagaatg agatgctgag ggaggagaac    360
aagaggcttg catccgcagc caagacttca ttttgccccct cctgcgttgc tttaccagga    420
ctgagtccct gggggaggt gcagaggcta aggcaggaaa acgagcaact gaagcaacag    480
ctctcacagc tgcgtgctga agcgcatcca agttcaagcc gtccttttca acttgaccca    540
tccatggaga atatcactgg aagagagaat gacatggatg cgattgctga actcgctcaa    600
agtgcaatgc acgagtttgt cgttctggcc gaagccggcg acctctgtg gatgcctgtc    660 cctggtggtt cctttgacgt gctgaacaag atggcttatg ctcaaacatt tggcgcaaga    720

```
agcagtgcaa atgtgatact aggattcatg accgaggcta ctcgtgctga tgacatggtc    780
atgatggacg ccaagcagat tgtggactac atcatggatt ctgagtgcta cacatctttc    840
tgtcctggac ttctgaccag tgcaaatacc accaagattt acaagtggcc taccagtgca    900
ggctacaatg gggctatgca tctggtgacc gtcgagacgg tgttcccatc accactggtg    960
ccatctagga aatgcacatt cgtgaggtgc tgcagggata tgcaaaatgg gacagtgatc   1020
atcgttgatg tgtctttgga caacggtgac ggcactgtca aatgccacaa aatgccatca   1080
ggagtgctag ttcggagcct gaattccgac gccagccagg tcactgtcat agagcatgtc   1140
caagtgaatg atactggtct tcacgagctc taccgcccaa gcttgagcgg actgatgttc   1200
ggagctaggc gctgggtgtc gagcatcgtg cgacaaagcg cacgcatgag agatctcttc   1260
gttgtcagca aaagcgcctc gaacggcaac acaaatggga ggaagaccct catgaagata   1320
gcggacggcc tgctcgcggg ctacgccagc ggcattgccg ccgtccctgg gggcggatgg   1380
accatcctgc gtggcgctgg cacggaagac gacatcagga tctcgtacag gaggaacaac   1440
gatgacagca acaccgccat cgtgtccgtg tgcgcgtcat tccatctgcc agtgccgcac   1500
agggtgacgt ttgatctgct caagaacaac ctgttgcgcc caaagtggga tgtgctggtg   1560
aacggtaatt cggtgaggga ggaagtcgct gtatgcaaag gcgtaggagg aggaattgat   1620
gatgttgtct ccatactgca tctcaaggat ccgcccaccg gggagaacag ggacaacatc   1680
atgatcctcc agaacagcag ctacgatgtg tcaggcgcgt tcatggtcta ctgcccagtc   1740
aacatccaac tgatgaatga gatcatgagc cccagcgaca cggcggagag caacaaggtg   1800
tccctctacc ccaccggctt ctacctcctc cccgtcgagg acactgccct tggcctcggc   1860
gagggtggag caactcttgt gaccgtgggg ttccagatta tgctcaagct cgctcgtggc   1920
accggcctgt atcctaggtc cgcgtccacg gccgtcggtc tgatgacaga aaacattgct   1980
accatcaaga agactctgac cagcagccac cccatcttct ataggaggca gcccccaac   2040
aatctcatct ag                                                        2052
```